United States Patent
Schiene et al.

(10) Patent No.: US 10,813,891 B2
(45) Date of Patent: Oct. 27, 2020

(54) METHOD OF INHIBITING CHRONIFICATION OF PAIN

(71) Applicant: Grünenthal GmbH, Aachen (DE)

(72) Inventors: Klaus Schiene, Juechen (DE); Ilona Steigerwald, Aachen (DE); Michel Hamon, Paris (FR); Johannes Schneider, Stolberg (DE); Silvia Reinartz, Aachen (DE); Ulrich Jahnel, Remscheid (DE); Thomas Tzschentke, Aachen (DE)

(73) Assignee: Grünenthal GmbH, Aachen (DE)

(*) Notice: Subject to any disclaimer, the term of this patent is extended or adjusted under 35 U.S.C. 154(b) by 0 days.

(21) Appl. No.: 16/516,856

(22) Filed: Jul. 19, 2019

(65) Prior Publication Data
US 2020/0009083 A1    Jan. 9, 2020

Related U.S. Application Data

(63) Continuation of application No. 15/243,271, filed on Aug. 22, 2016, now Pat. No. 10,398,657, which is a continuation of application No. 13/438,469, filed on Apr. 3, 2012, now abandoned.

(60) Provisional application No. 61/480,621, filed on Apr. 29, 2011, provisional application No. 61/471,919, filed on Apr. 5, 2011.

(30) Foreign Application Priority Data

Apr. 5, 2011  (EP) .................................... 11002811
Apr. 29, 2011 (EP) .................................... 11003508

(51) Int. Cl.
*A61K 31/137*  (2006.01)
*A61K 9/00*    (2006.01)
*A61P 25/04*   (2006.01)

(52) U.S. Cl.
CPC .......... *A61K 31/137* (2013.01); *A61K 9/0053* (2013.01); *A61P 25/04* (2018.01)

(58) Field of Classification Search
None
See application file for complete search history.

(56) References Cited

U.S. PATENT DOCUMENTS

| | | | |
|---|---|---|---|
| 4,612,008 A | 9/1986 | Wong et al. | |
| 4,765,989 A | 8/1988 | Wong et al. | |
| 4,783,337 A | 11/1988 | Wong et al. | |
| 6,248,737 B1 | 6/2001 | Buschmann et al. | |
| 7,868,043 B2 | 1/2011 | Yao et al. | |
| 10,398,657 B2* | 9/2019 | Schiene | |
| 2005/0058706 A1 | 3/2005 | Bartholomaeus et al. | |
| 2008/0269326 A1 | 10/2008 | Christoph et al. | |
| 2009/0012180 A1 | 1/2009 | Lange et al. | |
| 2009/0215809 A1 | 8/2009 | Yao et al. | |
| 2009/0306050 A1 | 12/2009 | Dinan | |
| 2010/0080797 A1 | 4/2010 | Yeomans et al. | |
| 2010/0227921 A1 | 9/2010 | Franklin et al. | |
| 2010/0280128 A1 | 11/2010 | Jahnel et al. | |
| 2010/0297181 A1 | 11/2010 | Hanada et al. | |
| 2010/0297229 A1 | 11/2010 | Sesha | |
| 2012/0309841 A1 | 12/2012 | Schiene et al. | |
| 2014/0027351 A1 | 1/2014 | Bazer-Bachi et al. | |

FOREIGN PATENT DOCUMENTS

| | | |
|---|---|---|
| DE | 10 2007 012 165 A1 | 9/2008 |
| EP | 0 693 475 A1 | 1/1996 |
| EP | 1 985 292 A1 | 10/2008 |
| JP | 2009-506076 A | 2/2009 |
| JP | 2010-531296 A | 9/2010 |
| JP | 2014-503020 A | 2/2014 |
| WO | 2007/025286 A2 | 3/2007 |
| WO | 2007/128412 A1 | 11/2007 |
| WO | 2008/110323 A1 | 9/2008 |
| WO | 2008/128740 A1 | 10/2008 |
| WO | 2009/067703 A2 | 5/2009 |
| WO | 2009/082039 A1 | 7/2009 |
| WO | 2012/136349 A1 | 10/2012 |

OTHER PUBLICATIONS

Hayes, C., et al., "Neuropathic Pain in the Perioperative Period", Int Anesthesiol Clin., 35(2): 67-81 (Spring 1997) (Fifteen (15) pages).
"Manual of Therapeutic Agents 2007", 2007, pp. 928-929 with English translation (9 pages).
Co-pending U.S. Appl. No. 13/438,410, Christoph et al., filed Apr. 3, 2012.
Co-pending U.S. Appl. No. 14/502,552, Steigerwald et al., filed Sep. 30, 2014.
Baron, "CME: Diagnosis and Treatment of Neuropathic Pain", Dtsch Arztebl, 2006, pp. 1-16, vol. 103, No. 41.
Stahl, "Preemptive Analgesia: Is Pain Less Costly When You Pre-Pay for It?", Clinical Neuroscience Update, 2004, pp. 1591-1592, Physicians Postgraduate Press, Inc.
Pergolizzi, et al., "The development of chronic pain: physiological Change necessitates a multidisciplinary approach to treatment"; CMRO vol. 29, No. 9, 2013, pp. 1127-1135.
Ossipov et al., "Descending pain modulation and chronification of pain"; Curr Opin Support Palliat Care. Jun. 2014, 8(2): pp. 143-151.
Niester et al.; "Tapentadol potentiates descending pain inhibition in chronic pain patients with diabetic polyneuropathy"; British journal of Anaesthesia 113 (1): p. 148-56 2014.

(Continued)

*Primary Examiner* — Savitha M Rao
*Assistant Examiner* — Gregg Polansky
(74) *Attorney, Agent, or Firm* — Norris McLaughlin, P.A.

(57) ABSTRACT

The use of tapentadol in the treatment of pain and/or pain chronification in a subject suffering from pain chronification and/or in the treatment of pain and inhibition of pain chronification in a subject suffering from pain and at risk of pain chronification, as well as the use of tapentadol for the treatment or inhibition of migraine.

6 Claims, 12 Drawing Sheets

(56) References Cited

OTHER PUBLICATIONS

McGreevy, et al.; "Preventing chronic pain following acute pain: risk factors, preventive strategies, and their efficacy"; Eur J. Pain Suppl Nov. 2011, 5(2): 365-372.
Puolakka PA, et al., Persistent pain following knee arthroplasty; Euro J Anaesthesiol, May 2010, 27(5); pp. 455-460—Abstract.
English Translation of ("Palexia® retard Retardtabletten", Gruenenthal GmbH, 2010, pp. 1-5, XP002G43G45—Thirteen (13) pages.
Alejandro Arana, et al., « Suicide-Related Events in Patients Treated with Antiepileptic Drugs The New England Journal of Medicine, Aug. 5, 2000, pp. 542-551.
Board of Appeals of EPO Decision May 4, 2000 Case No. T 0233/96-3.3.2.
Samuel F. Dworkin, et al. « Multiple Pains and Psychiatric Distrubance : An epidemiologic Investigation, Arch Gen Psychiatry, Mar. 1990, pp. 239-244, vol. 47.
Ezekiel Emanuel et al., "Euthanasia and Physician-Assisted Suicide: Attitudes and Experiences of Oncology patients, oncologists, and the Public", Department of Ethics, pp. 1805-1810, Jun. 29, 1996, vol. 347.
EPO Boards of Appeals, friction Reduction Additives Dec. 1989 Case No. G2/88.
European Search Report dated Jun. 21, 2011 EP 11 00 2811.
TJ Grudt, et al., "mu-Opioid Agonists Inhibit Spinal Trigeminal Substantia Gelatinosa Neurons in Guinea Pig and Rat", 1994, 1646-1645.
G. Magni et al., "Suicidality in Chronic Abdominal Pain : An Analysis of the Hispanic Health and Nutrition Examination Survey", Pain, 1998, pp. 137-144, vol. 76.
Vaugh E. Nossaman, et al., "Advances in Perioperative Pain Management: Use of Medications with Dual Analgesic Mechanisms, Tramadol & Tapentadol", Anesthesiology Clinics, 2010, pp. 647-666, vol. 28.
Palexia Filmtabletten, 2010 (Thirteen (13) pages).
Written Opinion dated May 7, 2013 (Int'l Preliminary Examining Authority—6 pages).
G. Richard Smith, "The Epidemiology and Treatment of Depression When it Coexists with Somatoform Disorders, Somatization or Pain", 1992, pp. 265-272.
Third Party Observation for Application No. EP20120718065 Jul. 12, 2016.
D. J. Williamson, et al., "Role of Opioid Receptors in Neurogenic Dural Vasodilation and Sensitization of Trigeminal Neurones Anaesthetized Rats", 2001, pp. 807-814.
Rathmel, J.P. et al., "Do you have the Tools to Prevent Phantom Limb Pain?", Anesthesiology, May 2011, pp. 1021-1024, vol. 114, No. 5.
"Palexia® retard Retardtabletten", Gruenenthal GmbH, 2010, pp. 1-5, XP002643645 (Five (5) pages).
Rauschkolb-Loeffler, C., et al., "Efficacy and Tolerability of Tapentadol for Relief of Moderate-to-Severe Chronic Pain Due to Osteoarthritis of the Knee", Annals of the Rheumatic Diseases, Jun. 16, 2007, p. 507, vol. 66, No. Suppl. 2, XP009101917 (One (1) page).
Evans, W. E., et al., "Pharmacogenomics: Translating Functional Genomics into Rational Therapeutics", Science, Oct. 15, 1999, pp. 487-491, vol. 286 (Six (6) pages).
Shipton, E. A., "The Transition from Acute to Chronic Post Surgical Pain", Anaesthesia and Intensive Care, Sep. 2011, pp. 824-836, vol. 39, No. 5 (Thirteen (13) pages).
Dahl, J. B., et al., "Preventive Analgesia", Current Opinion in Anesthesiology, 2011, pp. 331-338, vol. 24 (Eight (8) pages).
Lavand'Homme, P., "The Progression from Acute to Chronic Pain", Current Opinion in Anesthesiology, 2011, pp. 545-550, vol. 24 (Six (6) pages).
Rathmell, J. P., et al., "Do We Have the Tools to Prevent Phantom Limb Paing?", Anesthesiology, May 2011, pp. 1021-1024, vol. 114, No. 5 (Four (4) pages).

Macrae, W. A.,"Chronic Post-Surgical Pain: 10 Years On", British Journal of Anaesthesia, Apr. 22, 2008, vol. 101, No. 1, pp. 77-86 (Ten (10) pages).
Brennan, T. J., et al, "Characterization of a Rat Model of Incisional Pain", Pain, 1996, vol. 64, pp. 493-501 (Nine (9) pages).
Tzschentke, T. M., et al., "Tapentadol Hydrochloride", Drugs of the Future, 2006, vol. 31, No. 12, pp. 1053-1061, XP002438122 (Nine (9) pages).
Kehlet, H., et al., "Persistent Postsurgical Pain: The Path Forward through Better Design of Clinical Studies", Anesthesiology, Mar. 2010, vol. 112, No. 3, pp. 514-515 (Two (2) pages).
Extended European Search Report issued in counterpart European Application No. 11002811.5 dated Aug. 9, 2011 (Eight (8) pages).
Extended European Search Report issued in counterpart European Application No. 11002810.7 dated Jul. 1, 2011 (Eleven (11) pages).
Bennett, G. J., et al., "A Peripheral Mononeuropathy in Rat that Produces Disorders of Pain Sensation Like Those Seen in Man", Elsevier, Pain, 33, (1988), pp. 87-107 (Twenty-one (21) pages).
Lange, R., et al., "Short Form-36 (SF-36) and Euroqol-5 Dimension (EQ-5D) Results from Randomized, Double-Blind Phase 3 Studies of Tapentadol Prolonged Release (PR) in Patients with Moderate to Severe Chronic Nociceptive and Neuropathic Pain", vol. 18, Oct. 1, 2010, pp. S147-S148, XP027316899 (Two (2) pages).
Tzschentke, T. M., et al., "Tapentadol:Mitzwei Mechanismen in Einem Molekuel Wirksam Gegan Nozizeptive Und Neuropathische Schmerzen", vol. 25, No. 1, Feb. 1, 2011, pp. 19-25, XP009149538 (Seven (7) pages).
Schroeder, W., et al., "Differential Contribution of Opioid and Noradrenergic Mechanisms of Tapentadol in Rat Models of Nociceptive and Neuropathic Pain", European Journal of Pain, vol. 14, No. 8, Sep. 1, 2010, pp. 814-821, XP027224271 (Eight (8) pages).
Christoph, T., et al., "Anti-Allodynic Activity of Tapentadol in a Rat Model of Neuropathic Pain Depends on Opioid and Noradrenergic, But Not Serotonergic, Mechanisms", European Journal of Pain, vol. 13, Sep. 1, 2009, p. S205 (One (1) page).
Kayser, V., et al., "Differential Anti-Neuropathic Pain Effects of Tetrodotoxin in Sciatic Nerve-Versus Infraorbital Nerve-Ligated Rats—Behavioral, Pharmacological and Immunohistochemical Ivestigations", Neuropharmacology, vol. 58, (2010) pp. 474-487 (Fourteen (14) pages).
Vos, B. P., et al., "Behavioral Evidence of Trigeminal Neuropathic Pain Following Chronic Constriction Injury to the Rat's Infraorbital Nerve", The Journal of Neuroscience, vol. 14, No. 5, May 1994, pp. 2708-2723 (Sixteen (16) pages).
Kayser, V., et al., "The Antimigraine 5-HT 1B/1D Receptor Agonists, Sumatriptan, Zolmitriptan and Dihydroergotamine, Attenuate Pain-Related Behaviour in a Rat Model of Trigeminal Neuropathic Pain", British Journal of Pharmacology, vol. 137, (2002), pp. 1287-1297 (Eleven (11) pages).
Wang, X., et al., "TrkB Signaling is Required for Both the Induction and Maintenance of Tissue and Nerve Injury-Induced Persistent Pain", The Journal of Neuroscience, vol. 29, No. 17 Apr. 29, 2009, pp. 5508-5515 (Eight (8) pages).
Merighi, A., et al., "BDNF as a Pain Modulator", Progress in Neurobiology, vol. 85, (2008), Elsevier, pp. 297-317 (Twenty-one (21) pages).
Partial International Search Report (PCT/ISA/206) issued in PCT application No. PCT/EP2012/001472 dated Jun. 6, 2012 (Five (5) pages).
Liang, et al.; "Chronic morphine administration enhances nociceptive sensitivity and local cytokine production after incision"; Molecular Pain 2008, 4:7, pp. 1-12.
Gore, et al.; "Pain Severity in Diabetic Peripheral Neuropathy is Associated with Patient Functioning, Symptom Levels of Anxiety and Depression, and Sleep"; Journal of Pain and Symptom Management vol. 30, No. 4, Oct. 2005, pp. 374-385.
International Search Report (PCT/ISA/210) issued in PCT application No. PCT/EP2012/001472 dated Aug. 3, 2012 (Six (6) pages).
Written Opinion (PCT/ISA/237) issued in PCT application No. PCT/EP2012/001472 dated Aug. 3, 2012 (Thirteen (13) pages).
Pergolizzi Jr., J., et al., "Treating Acute Pain in Light of the Chronification of Pain", Pain Management Nursing, vol. 15, No. 1, Mar. 2014, pp. 380-390 (Eleven (11) pages).

(56) References Cited

OTHER PUBLICATIONS

Pergolizzi Jr., J., et al., "Treating Acute Pain in Light of the Chronification of Pain," Pain Management Nursing, 2012, pp. 1-11 (Eleven (11) pages).
Vadivelu et al., Yale Journal of Biology and Medicine, Mar. 2010, vol. 83, pp. 11-25 (Fifteen (15) pages).
Tzschentke, T., et al., "(−)-(1R, 2R)-3-(3-Dimethylamino-1-ethil-2-methyl-propyl)-phenol Hydrocloride (Tapentadol HCl): a Novel gamma-Opioid Receptor Agnonist/Norepinephrine Reuptake Inhibitor with Broad-Spectrum Analgesic Properties", The Journal of Pharmacology and Experimental Therapeutics, 2007, vol. 323, No. 1, pp. 265-276 (Twelve (12) pages).
Perkins et al., "Chronic Pain as an Outcome of Surgery", Anesthesiology, 2000, vol. 93, pp. 1123-1133 (Eleven (11) pages).
Afilalo, M., et al. Efficacy and Saftey of Tapentadol Extended Release Compared with Oxycodone Controlled Release for the Management of Moderate to Severe Chronic Pain Related to Osteoarthritis of the Knee: A Randomized, Double-Blind, Placebo- and Active Controlled Phase III Study:, Clinical Drug Investigation, Aug. 1, 2010, pp. 489-505, vol. 30, No. 8, XP009148168 (Seventeen (17) pages).
Kuperwasser, B., et al., "337 Evaluation of Long-Term Treatment with Tapentadol Extended Release and Oxycodone Controlled Release in Patients with Chronic Low Back or Osteoarthritis Pain: Results from Patient and Physician Global Assessments and the Euroqol 5 Dimension Questionnaire", Osteoarthritis and Cartilage, Sep. 1, 2009, p. S179, vol. 17, Supplement 1, XP026582221 (One (1) page).
Kuperwasser, B., et al., "337 Health Status of Patients Who Received Tapentadol Prolonged Release During an Open-Label Extension Study", Osteoarthritis and Cartilage, Oct. 1, 2010, p. S149, vol. 18, XP027316893 (One (1) page).
Schwartz, S., et al., "Safety and efficacy of Tapentadol ER in Patients with Painful Diabetic Peripheral Neuropathy: Results of a Randomized-Withdrawal, Placebo-Controlled Trial", Current Medical Research & Opinion, Jan. 2011, vol. 27, No. 1, pp. 151-162, XP009150479 (Twelve (12) pages).
Extended European Search Report issued in counterpart European Application No. 11003508.6 dated Jul. 28, 2011 (Eight (8) pages).
Ali, R.A., "Management of Diabetic Neuropathy," Malaysian Journal of Medical Sciences, 2003, vol. 10, No. 2, pp. 27-30 (Four (4) pages).
Vileiktye, L., et al., "Diabetic Peripheral Neuropathy and Depressive Symptoms," Diabetes Care, 2005, vol. 28, pp. 2378-2383 (Six (6) pages).
"Tapentadol and its two mechanisms of action: Is there a new pharmacological class of centrally-acting analgesics on the horizon?" European Journal of Pain, 2010, vol. 14, pp. 781-783 (Three (3) pages).
Latremoliere et al., "Differential Implication of Proinflammatory Cytokine Interleukin-6 in the Development of Cephalic versus Extracephalic Neuropathic Pain in Rats", The Journal of Neuroscience 28(34), Aug. 20, 2008, pp. 8489-8501 (Thirteen (13) pages).
Ravin, L. Ph.D., "Preformulation", Remington Chapter 76, 1985, pp. 1409-1423 (Fifteen (15) pages).
Disanto, A., "Bioavailability and Bioequivalency Testing", Remington Chapter 77, 1985, pp. 1424-1431 (Eight (8) sheets).
Knevel, A. Ph.D., "Separation", Remington Chapter 78, 1985, pp. 1432-1442 (Eleven (11)pages).
Phillips, G. B., Ph.D., "Sterilization", Remington Chapter 79, 1985, pp. 1443-1454 (Twelve (12) pages).
Siegel, F., Ph.D., "Tonicity, Osmoticity, Osmolality and Osmolarity", Remington Chapter 80, 1985, pp. 1455-1472 (Eighteen (18) pages).
Giles, R., et al., "Plastic Packaging Materials", Remington Chapter 81, 1985, pp. 1473-1477 (Five (5) pages).
Lintner, C., Ph.D., "Stability of Pharmaceutical Products", Remington Chapter 82, 1985, pp. 1478-1486, (Nine (9) pages).
Erskine Jr., C., "Quality Assurance and Control" Remington Chapter 83, 1985, pp. 1487-1491 (Five (5) pages).
Nairn, J.G., Ph.D., "Solutions, Emulsions, Suspensions and Extractives", Remington Chapter 84, 1985, pp. 1492-1517 (Twenty-six (26) pages).
Avis, K. E., DSc., "Parenteral Preparations", Remington Chapter 85, 1985, pp. 1518-1541 (Twenty-four (24) page).
Turco S. J., et al., "Intravenous Admixtures", Remington Chapter 86, 1985, pp. 1542-1552 (Eleven (11) pages).
Mullins, J. D., Ph.D., "Ophthalmic Preparations", Remington Chapter 87, 1985, pp. 1553-1566 (Fourteen (14) pages).
Block, L. H., Ph.D., "Medicated Applications", Remington Chapter 88, 1985, pp. 1567-1584 (Eighteen (18) pages).
Rippie, E. G., Ph.D., "Powders", Remington Chapter 89, 1985, pp. 1585-1602 (Eighteen (18) pages).
King, R. E., et al., "Oral Solid Dosage Forms", Remington Chapter 90, 1985, pp. 1603-1632 (Thirty (30) pages).
Porter, S. C., Ph.D., "Coating of Pharmaceutical Dosage Forms", Remington Chapter 91, 1985, pp. 1633-1643 (Eleven (11) pages).
Longer, M. A., et al., "Sustained-Release Drug Delivery Systems", Remington Chapter 92, 1985, pp. 1644-1661 (Eighteen (18) pages).
Sclarra, J. J., Ph.D., et al., "Aerosols", Remington Chapter 93, 1985, pp. 1662-1677 (Sixteen (16) pages).
Daniels, S., et al., "A randomized, double-blind, placebo-controlled phase 3 study of the relative efficacy and tolerability of tapentadol IR and oxycodone IR for acute pain", Current Medical Research and Opinions, 2009, pp. 1551-1561, vol. 25, No. 6, Premier Research et al., Austin, TX.
Masuda, Y., The Journal of Japanese Society for the Study of Chronic Pain, 2006, pp. 23-27, vol. 25, No. 1, Presented by Medical Online, Department of Anesthesiology, Showa University School of Medicine, with English abstract and translation (Twelve (12) pages).
Kodama, K., et al., "Post-surgical Pain Control", The Japanese Journal of Clinical and Experimental Medicine, 2001, vol. 78, No. 3, pp. 91-94, with English translation (Twelve (12) pages).
Kobayashi, N., et al., "Clinical Pearl of Psychosomatic Medicine for Gastrointestinal Disorders", Jpn J Psychosom Med, 2010, pp. 1045-1050, vol. 50, No. 11, Presented by Medical Online, with English abstract and translation (Fifteen (15) pages).
Rathmell, J. P., et al., "Do We Have the Tools to Prevent Phantom Limb Pain?", Anesthesiology, May 2011, pp. 1021-1024, vol. 114, No. 5 (Four (4) pages).
International Search Report (PCT/ISA/220 & PCT/ISA/210) issued in PCT Application No. PCT/EP2012/001475 dated Jun. 27, 2012 (Six (6) pages).
Written Opinion (PCT/ISA/237) issued in PCT Application No. PCT/EP2012/001475 dated Jun. 27, 2012 (Five (5) pages).
Shou, W.T., et al., "314 Oral Raffinamide Suppresses Autonomy Following Hindpaw Deafferentation by Multiple Dorsal Rhizotomies, a Rat Model of CNS-Mediated Spontaneous Neuropathic Pain", Poster Sessions/European Journal of Pain, 2009, vol. 13, pp. S96-S97, XP 26680911 (Two (2) pages).
Bjelland, I., et al., "The Validity of the Hospital Anxiety and Depression Scale—An Updated Literature Review" Journal of Psychosomatic Research, 2002, vol. 52, pp. 69-77.
Nadaoka, T., "Diagnosis of Pain Disorder Based on Clinical Psychiatry", Pain and Clinical Treatment, 2001, vol. 1(2), No. 3, pp. 111 with partial English translation (Two (2) pages).
Motoshima, A., "Experiences of Cases Associated with Pain", Clinical Psychiatry, Dec. 1996, vol. 25, p. 1493 with partial English translation (Two (2) pages).
Nakamura, H., "Pain and Heart", Dental Diamond, 1999, vol. 24 (338), p. 76 with partial English translation (Two (2) pages).
Tanaka, C., et al., "New Pharmacology", published by Nankodo, 1997, Chapter 5, p. 282 with partial English translation (Two (2) pages).
Wild, J.E., et al., "Long-term safety and tolerability of tapentadol extended release for the management of chronic low back pain or osteoarthritis pain", Abstract, Pain Pract. Sep.-Oct. 2010; 10(5); URL retrieved from: http://www.ncbi.nlm.nih.gov/pubmed/?term=20602712=Abstract dated Jul. 7, 2016 (Two (2) pages).
Third Party Observation for Application No. EP 20120718064 dated Jul. 7, 2016 (Four (4) pages).

(56) References Cited

OTHER PUBLICATIONS

The U.S. Food and Drug Administration approved NUCYNTA (Tapentadol) Medication Guide, revised Jun. 2010, PriCara, Division of Ortho-McNeil-Janssen Pharmaceuticals, Inc., Reference ID: 2858116 (Twenty-six (26) pages).

Wilder-Smith, et al; "Postoperative Hyperalgesia"; Anesthesiology, vol. 104; No. 3; Mar. 2006; pp. 601-607.

Lehmann, Klaus A.; "Recent Developments in Patient-Controlled Analgesia"; Journal of Pain and Symptom Management; vol. 29, No. 5S, May 2005; pp. S72-S89.

Hegarty, Dominic; "The long-term teratment of atypical odontalgia with tapentadol: a case report": International Journal of Dentistry and Oral Health; 2017, vol. 3.2; pp. 1-3.

Christensen et al. "Combined systemic administration of the glycine/NMDA receptor antagonist, (+)-HA966 and morphine attenuates pain-related behaviour in a rat model of trigeminal neuropathic pain"; Pain 83 (1999) pp. 433-440.

Freye; "Opioids in Medicine A Comprehensive Review on the Mode of Action and the Use of analgesics in Different Pain States" 2008, pp. 1-13 and 50-65.

Etropolski, Mila; "Safety and Tolerability of Tapentadol Extended Release (ER) in Patients with Painful Diabetic Peripheral Neuropathy (DPN): Results of a Randomized-Withdrawal Phase 3 Study"; American Diabetes Association 2009 https://professional.diabetes.org/abstract/safety-and-tolerability-tapentadol-extended-release-er-patients-painful-diabetic-peripheral.

Highlights of Prescribing Information; NUCYNTA, 2010.

Cephalalgia an International Journal of Headache; the International Classification of Headache Disorders 2nd Edition; vol. 24, Supplement 1, 2004 pp. 126-135.

Jaggi et al., "Animal models of neuropathic pain"; Fundamental & Clinical Pharmacology 2011, 1-28.

Zakrzewska; "Medical management of trigeminal neuropathic pains"; Expert Opinion Pharmacother, 2010, 11(8); pp. 1239-1254.

\* cited by examiner

METHOD OF INHIBITING CHRONIFICATION OF PAIN

CROSS REFERENCE TO RELATED APPLICATIONS

This application is a continuation of U.S. application Ser. No. 15/243,271, filed Aug. 22, 2016, now allowed; which is a continuation of U.S. application Ser. No. 13/438,469, filed on Apr. 3, 2012, now abandoned, which claims priority to U.S. provisional patent application Nos. 61/471,919 and 61/480,621, filed Apr. 5, 2011 and Apr. 29, 2011, respectively, the entire disclosures of all of which are incorporated herein by reference. Priority is also claimed to European patent application nos. EP 11 002 811.5 and EP 11 003 508.6, filed Apr. 5, 2011 and Apr. 29, 2011, respectively, the entire disclosures of each of which are likewise incorporated herein by reference.

BACKGROUND OF THE INVENTION

The invention relates to tapentadol for use in the treatment of pain in a subject suffering from pain chronification and/or for use in the treatment or the inhibition of pain chronification. The invention also relates to tapentadol for use in the treatment or inhibition of migraine, i.e. of migraine-related pain, and headache-related pain.

Tapentadol (CG5503), the chemical name for which is (−)-(1R,2R)-3-(3-dimethylamino-1-ethyl-2-methyl-propyl)-phenol, is a synthetic, centrally-acting analgesic that is effective for the treatment of moderate to moderately-severe acute or chronic pain. The compound can be employed as the free base or its pharmaceutically acceptable salts and solvates. Preparation of the free base is known from EP-A 693 475.

Tapentadol is a centrally acting analgesic with a dual mode of action consisting of μ-opioid receptor (MOR) agonism and norepinephrine (NE) reuptake inhibition. The efficacy, safety, and pharmacokinetic profile of tapentadol indicate that the drug is useful in treating acute as well as chronic pain. The mixed μ-opioid receptor agonist/noradrenaline reuptake inhibitor, tapentadol, was found to reduce acute and chronic pain in validated animal models. However none of these models involved pain at cephalic level.

The activity of tapentadol is independent of metabolic activation and resides in a single enantiomer which readily crosses the blood-brain barrier; hence, tapentadol displays a rapid onset of action after administration. The biotransformation of tapentadol by metabolic enzymes results in deactivation, i.e., tapentadol has no active metabolites, and the main metabolic pathway for elimination is phase II glucuronidation. Phase I biotransformations such as hydroxylation and N-demethylation play only a minor role in the metabolic fate of tapentadol. Owing to the minor involvement of phase I metabolic pathways, tapentadol has a low potential for drug-drug interactions and interindividual variability (cf. Tzschentke T. M. et al. Tapentadol Hydrochloride. *Drugs of the Future* 2006, 31, 1053-1061; Evans W. E., Relling, M. V. Pharmacogenomics: Translating Functional Genomics into Rational Therapies. *Science* 1999, 286, 487-491).

EP 1 985 292 relates to titration regimens of tapentadol. The official expert information concerning Palexia®, a commercial product containing tapentadol, indicates that tapentadol is for treating chronic pain. Rauschkolb-Loeffler et al., Annals of the rheumatic diseases, 2007, 507 relates to a clinical trial concerning treatment of chronic pain due to osteoarthritis of the knee.

Chronic pain due to chronification of pain, however, is not synonymous to chronic pain in general; not every chronic pain is a result of pain chronification. Instead, chronic pain due to chronification of pain is a sub-type of chronic pain. Chronification of pain is the conversion of acute pain into chronic pain. It is known that therapy of acute pain, e.g. postoperative pain (postsurgical pain), by means of conventional analgesics can result in chronification of pain. In consequence, pain sensation last longer than would typically be expected in view of progressing postoperative wound healing; even though wound healing has been nearly completed, the patient still suffers from pain. Chronification of pain can lead to e.g. persistent postsurgical pain (PPP), also referred to as chronic post-surgical pain (CPSP), which the International Association for the Study of Pain defined as a persistent pain state that is apparent for more than 2 months postoperatively and cannot be explained by other causes (recurrence of disease, inflammation, and others).

Chronic postoperative pain has estimated incidences of 30-50% after amputation, 20-30% after breast surgery, 30-40% after thoracotomy, about 10% after inguinal hernia repair, 30-50% after coronary artery bypass surgery, and about 10% after Cesarean section. Patients suffering from chronic pain are typically characterized by wide spread pain, a long lasting medical history, psycho-social problems as well as many unsuccessful treatments. For further details, it can be referred to e.g. W. A. Macrae, British Journal of Anaesthesia 101(1): 77-86 (2008); T. J. Brennan, Anesthesiology, 2010, 112:514-5; J. P. Rathmell et al., Anesthesiology, 2011, 114:1021-4; P. Lavand'homme, Curr Opin Anesthesiol 2011, 24:545-550; J. B. Dahl et al., Curr Opin Anesthesiol 2011, 24:331-338; E. A. Shipton, Anaesth Intensive Care 2011; 39, 824-836.

It is assumed that every nociceptive stimulus which acts on the central nervous system is capable of reinforcing pain in the long term thus leading to a chronification of pain. If corresponding stimuli are maintained for a prolonged time period, the synaptic transmission is amplified through a process called "long term potentiation," resulting in pain chronification. Chronification processes are neuronal conduction processes caused by the plasticity of neuronal functions. The plasticity of neuronal functions allows for a mechanism called "wind up" in which subsequently incoming impulses are amplified. However, chronification of pain is not just a simple matter of duration. Chronification is more a spread of pain on the physical level, on duration and even more on the psychological and social levels. Evaluation of the amount of chronification may be based e.g. on the graduation of chronic pain by von Korff. Chronicity of pain correlates with quality of life and effectiveness of medical treatment.

On the one hand, mechanisms can be peripheral, i.e. primary afferent nociceptor sensitation, e.g., due to spontaneous activity, decreased threshold, increased response to suprathreshold stimulants, recruitment of silent nociceptors, and the like. On the other hand, mechanisms can also be central, i.e. central sensitization, e.g., due to enhanced synaptic excitability (dorsal root ganglia, dorsal horn), expansion of receptor fields, altered mood and autonomic reflexes in the limbic system and hypothalamus, activation of spinal circuits from brainstem, and the like.

As far as chronic post-surgical pain is concerned, many physicians believe that pain around the time of an operation sensitizes the nervous system and this hypersensitized state contributes to the development of chronic pain. Unfortunately, the evidence for the effect of different anaestetic and analgesic regimens on chronic pain after surgery is confused. Several studies show benefit from regional anaestesia, for example, after hysterectomy, Cesarean section, iliac crest bone harvesting, and thoractomy. There are also studies, however, that have not shown benefit. Several studies have looked at multimodal analgesic techniques and the use of drugs such as gabapentin, venlafaxine, and ketamine, but once again the results are not consistent (cf. W. A. Macrae, British Journal of Anaethesia 2008, 101(1), 77-86).

It is known that conventional opioid analgesics can detrimentally influence the development of chronic pain. For example, L. DeYoung et al., Molecular Pain, 2008, 4(7), 1-12 report that morphine does not inhibit incision-induced hyperalgesia in mice hindpaw 24 h after incision, i.e. surgery. While in mice treated with brine hyperalgesia decreases 72 h after incision, hyperalgesia is even maintained in mice treated with morphine. Thus, as far as the inhibition of postoperative hyperalgesia in mice is concerned, morphine does have no advantageous effect or even is disadvantageous.

There is a demand for medicaments that are useful for treating or inhibiting the chronification of pain and that are useful for treating pain in subjects suffering from chronification of pain.

Neuropathic pain is a major problem for clinicians, as available treatments produce incomplete pain relief, and have dose-limiting side effects. Besides, neuropathic pain in territories innervated by the trigeminal system ("cephalic" territories) is even more difficult to treat than that in other parts of the body ("extracephalic" territories). Indeed, neuropathic pain symptoms in cephalic versus extracephalic territory are differentially attenuated by drugs. Previous investigations in rat models of chronic constriction injury to the sciatic nerve (CCI-SN) or the infraorbital nerve (CCI-ION) showed that morphine at low dose, tricyclic antidepressants and tetrodotoxin reversed allodynia/hyperalgesia in the hindpaw in CCI-SN rats but were inactive against allodynia in the vibrissae territory in CCI-ION rats.

Conversely, anti-migraine drugs such as triptans and CGRP receptor antagonists significantly reduced allodynia in CCI-ION rats but were inactive in CCI-SN rats. Further investigations also showed that physiopathological mechanisms underlying neuropathic pain differed in CCI-SN vs CCI-ION rats. In particular, CCI-SN was found to trigger interleukin-6 (IL-6) production in the ipsilateral dorsal horn of the lumbar spinal cord whereas no IL-6 induction could be detected in the spinal nucleus of the trigeminal nerve (Sp5c) in CCI-ION rats.

A potential strategy for enhancing the efficacy of pharmacological treatments without causing further undesirable side effects can be the use of drug combinations. Notably, in CCI-ION rats, it has been demonstrated that the combined administration of the glycine/NMDA receptor antagonist (+)-HA966 and morphine attenuated cephalic neuropathic pain although each drug alone was inactive.

With regard to chronic pain, tapentadol has been shown to exert clear-cut antihyperalgesic/antiallodynic effects in rats suffering from neuropathic pain caused by streptozotocin administration (diabetic polyneuropathy), spinal nerve ligation or CCI-SN. However, all these models concerned neuropathic pain in extracephalic territories, and none is known yet regarding the potential antiallodynic/antihyperalgesic effects of tapentadol in cephalic territories.

There is a need for medicaments that are useful for treating or inhibiting migraine.

SUMMARY OF THE INVENTION

It is an object of the invention to provide medicaments and medications having advantages compared to the prior art.

This and other objects are achieved by the invention as described and claimed hereinafter.

It has been surprisingly found that tapentadol does not show a pronounced tendency of developing chronification of pain. Thus, tapentadol is particularly useful in the treatment of pain in a subject suffering from pain chronification and/or for use in the treatment or the inhibition of pain chronification.

Further, it has been surprisingly found that tapentadol is useful in the treatment and inhibition of migraine. In contrast to most analgesic drugs which differently reduce neuropathic pain in cephalic versus extracephalic territories, tapentadol has been found equally effective in both territories. Its effect surprisingly involves synergy between the two pharmacological actions of tapentadol, particularly at cephalic level.

DESCRIPTION OF THE INVENTION

Figure 1:
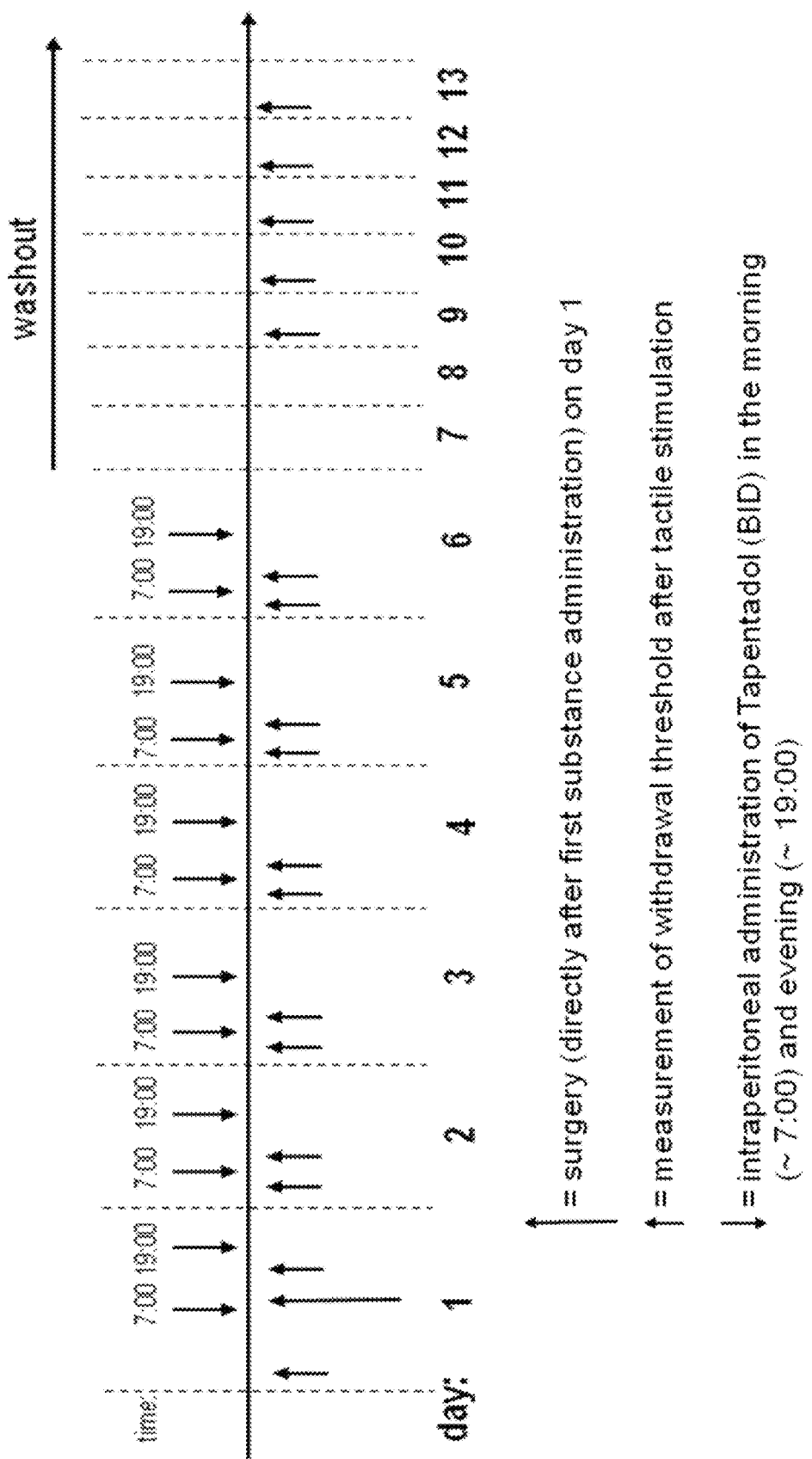
FIG. 1 shows a study scheme. Tapentadol at the dose of 14.7 mg/kg intraperitoneal route (i.p.) was adminstered twice daily (BID) (7 a.m./7 p.m.) throughout day 1 to day 5. The first administration was given 20 min before surgery on day 1. From day 6 to day 13 no substance was given (wash out phase)

A first aspect of the invention relates to tapentadol for use in the treatment of pain, preferably in a subject suffering from pain chronification and/or for use in the treatment or the inhibition of pain chronification.

Thus, the invention relates to, inter alia, tapentadol for use in the
(i) treatment of pain in a subject suffering from pain chronification (treatment of chronic pain due to pain chronification, treatment of chronified pain);
(ii) treatment of pain chronification in a subject suffering from pain chronification;
(iii) inhibition of pain chronification;
(iv) treatment of pain and the simultaneous treatment of pain chronification in a subject suffering from pain chronification; and
(v) treatment of pain and simultaneous inhibition of pain chronification.

A second aspect of the invention relates to a method for the treatment of pain in a subject suffering from pain chronification and/or for the treatment or the inhibition of pain chronification comprising the administration of an effective amount of tapentadol.

A third aspect of the invention relates to tapentadol for use in the treatment of migraine.

A fourth aspect of the invention relates to a method for the treatment of migraine comprising the administration of an effective amount of tapentadol to a subject in need thereof.

For the purpose of the specification, "tapentadol" is intended to include (−)-(1R,2R)-3-(3-dimethylamino-1-ethyl-2-methyl-propyl)-phenol, its pharmaceutically acceptable salts and solvates thereof. Suitable pharmaceutically acceptable salts include salts of inorganic acids, such as hydrochloric acid (tapentadol HCl), hydrobromic acid and sulfuric acid, and salts of organic acids, such as methane sulfonic acid, fumaric acid, maleic acid, acetic acid, oxalic acid, succinic acid, malic acid, tartaric acid, mandelic acid, lactic acid, citric acid, glutamic acid, acetylsalicylic acid, nicotinic acid, aminobenoic acid, α-liponic acid, hippuric acid and asparaginic acid. The preferred salt is the hydrochloride salt.

As used herein, the terms "inhibit" or "inhibition" refer to a reduction, lessening or retarding effect.

For the purpose of the specification, doses of tapentadol relate to the free base. Thus, when a pharmaceutically acceptable salt is used instead, its dose has to be adapted to the equivalent dose of the free base. For example, a dose of "200 mg" means an amount of 200 mg of the free base or any equivalent amount of a pharmaceutically acceptable salt or solvate corresponding to 200 mg of the free base (e.g. about 233 mg of the hydrochloride). If not expressly stated otherwise, doses are "per administration", not "per day".

According to the invention, tapentadol is used in the treatment of pain in a subject suffering from pain chronification and/or in the treatment or the inhibition of pain chronification. Preferably, the pain to be treated and/or the chronification of which is to be inhibited is moderate or severe and can preferably be central or peripheral. In a preferred embodiment, the pain is acute. Preferably, the acute pain is selected from the group consisting of mechanical pain, heat pain, cold pain, ischemic pain, and chemical-induced pain.

For the purpose of the specification, pain chronification leads to a chronic pain state (chronified pain, persistent pain). Preferably, said chronic pain state is due to a conversion, namely pain chronification, of an earlier, non-chronic pain state, which as such, at its origin, was neither qualified as being chronic nor expected to become chronic under usual circumstances. In other words, pain chronification in the meaning of the invention preferably transforms a non-chronic pain state into a chronic pain state, although the stimulus of the original non-chronic pain state as such was non-chronic in the beginning. Chronification of pain is typically observed only in a subpopulation of patients initially suffering from said non-chronic pain state. Therefore, not each and every patient suffering from said non-chronic pain automatically develops a chronification thereof.

When tapentadol is for use in the treatment of pain in a subject suffering from pain chronification, the pain to be treated typically includes chronic pain due to pain chronification, i.e. a chronic pain state that is a result of a chronification process which has converted an originally non-chronic pain state (e.g. an acute pain state) into said chronic pain state (=chronified pain), even though the pain stimulus that has originally induced said non-chronic pain state does not exist any longer or at least does not explain the degree of chronic pain the patient still suffers from. Thus, according to this embodiment of the invention, pain chronification has already taken place.

When tapentadol is for use in the treatment of pain chronification in a subject suffering from pain chronification, an ongoing chronification process is about to convert a non-chronic pain state into a chronic pain state (=chronified pain), even though the pain stimulus that has originally induced said non-chronic pain state does not exist any longer or at least does not explain the degree of chronic pain the patient still suffers from. Thus, according to this embodiment of the invention, pain chronification is going on.

When tapentadol is for use in the inhibition of pain chronification, a chronification process has typically not commenced, i.e. the pain state is still non-chronic (e.g. acute). Thus, according to this embodiment of the invention, pain chronification has not (yet) taken place.

A skilled person recognizes that a patient may suffer from different pain states simultaneously and that therefore the above situations (i), (ii) and (iii) may superimpose one another.

For the purpose of the specification, it can be distinguished between pain stimuli typically inducing non-chronic pain (e.g. surgery) and pain stimuli typically inducing chronic pain (e.g. osteoarthritis). Under usual circumstances, non-chronic pain caused by stimuli typically inducing non-chronic pain disappears when the stimuli has disappeared (e.g. when after surgery wound healing has reached a certain degree). Under the specific circumstances of pain chronification, however, the pain does not disappear, although the stimuli has disappeared, thereby transforming the non-chronic pain into chronic pain (chronified pain).

In a preferred embodiment, the pain to be treated and/or the chronification of which is to be inhibited is selected from the group consisting of headache, facial pain, pain in vascular diseases, neuropathic pain, spinal pain, musculoskeletal pain, visceral pain, posttraumatic pain and pain without somatic cause.

In another preferred embodiment, the pain to be treated and/or the chronification of which is to be inhibited is selected from the group consisting of postoperative pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, and chemotherapy-induced pain.

In another preferred embodiment, the pain to be treated and/or the chronification of which is to be inhibited is selected from the group consisting of pain due to arthrosis, pain due to intervertebral disc disorder, other specific back pain, neuropathic pain, non-specific back pain, headache, pain after traumatic fractures, pain of multimorbid high maintenance patients, and cancer pain.

In still another preferred embodiment, the pain to be treated and/or the chronification of which is to be inhibited is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; non-organic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [I20.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10.

In another aspect, the invention relates to the inhibition or treatment of pain selected from the aforementioned list of forms of pain according to ICD-10, preferably migraine, trigeminal neuralgia and other types of cephalic neuropathic pain, irrespective of whether the subject simultaneously suffers from chronification of pain or not. In an especially preferred embodiment, the invention relates to the inhibition or treatment of migraine [G43].

For the purpose of the specification, migraine preferably includes migraine-related pain.

In a preferred embodiment, the subject suffering from migraine simultaneously suffers from chronification of pain. In another preferred embodiment, the subject suffering from migraine does not simultaneously suffer from chronification of pain.

Preferably, tapentadol is administered via a route selected from the group consisting of orally, buccally, sublingually, transmucosally, intralumbally, intraperitoneally, transdermally, intravenously, intramusculously, intragluteally, intracutaneously and subcutaneously. Most preferably, however, tapentadol is administered orally.

Preferably, tapentadol is administered once daily or twice daily.

Preferably, tapentadol is administered at a daily dose within the range of from 25 to 600 mg.

In a preferred embodiment, the dose of tapentadol to be administered once daily or twice daily in the course of each administration amounts to 50 mg (±75%), more preferably 50 mg (±50%), still more preferably 50 mg (±30%), yet more preferably 50 mg (±20%), most preferably 50 mg (±10%), and in particular 50 mg (±5%).

In another preferred embodiment, the dose of tapentadol to be administered once daily or twice daily in the course of each administration amounts to 100 mg (±75%), more preferably 100 mg (±50%), still more preferably 100 mg (±30%), yet more preferably 100 mg (±20%), most preferably 100 mg (±10%), and in particular 100 mg (±5%).

In still another preferred embodiment, the dose of tapentadol to be administered once daily or twice daily in the course of each administration amounts to 150 mg (±75%), more preferably 150 mg (±50%), still more preferably 150 mg (±30%), yet more preferably 150 mg (±20%), most preferably 150 mg (±10%), and in particular 150 mg (±5%).

In yet another preferred embodiment, the dose of tapentadol to be administered once daily or twice daily in the course of each administration amounts to 200 mg (±75%), more preferably 200 mg (±50%), still more preferably 200 mg (±30%), yet more preferably 200 mg (±20%), most preferably 200 mg (±10%), and in particular 200 mg (±5%).

In a preferred embodiment, the dose of tapentadol to be administered once daily or twice daily in the course of each administration amounts to 250 mg (±75%), more preferably 250 mg (±50%), still more preferably 250 mg (±30%), yet more preferably 250 mg (±20%), most preferably 250 mg (±10%), and in particular 250 mg (±5%).

Preferably, tapentadol is administered once or twice daily, but not longer than for 31 days, more preferably not longer than for 28 days, still more preferably not longer than for 25 days, yet more preferably not longer than for 21 days, most preferably not longer than for 18 days and in particular not longer than for 14 days.

In a preferred embodiment, the pain to be treated or the chronification of which to be inhibited is acute pain and tapentadol is administered during $M_1$ consecutive days of a phase $O_1$, optionally in combination with another analgesic, but not during $M_2$ consecutive days of a phase $O_2$ directly following said phase $O_1$;

wherein $M_1$ and $M_2$ are independently an integer of from 1 to 100, preferably with the proviso that $M_2 \geq M_1$.

Preferred embodiments $D^1$ to $D^{12}$ of phases $O_1$ and $O_2$ are summarized here below:

| days | $D^1$ | $D^2$ | $D^3$ | $D^4$ | $D^5$ | $D^6$ | $D^7$ | $D^8$ | $D^9$ | $D^{10}$ | $D^{11}$ | $D^{12}$ |
|---|---|---|---|---|---|---|---|---|---|---|---|---|
| $O_1/M_1$ | ≥1 | ≥1 | ≥2 | ≥2 | 2-14 | 2-14 | 3-10 | 3-10 | 4-7 | 4-7 | 4-7 | 4-7 |
| $O_2/M_2$ | ≥7 | ≥7 | ≥7 | ≥7 | ≥10 | ≥10 | ≥10 | ≥10 | ≥14 | ≥14 | ≥14 | ≥14 |

In a preferred embodiment, the pain to be treated or the chronification of which to be inhibited is acute pain, preferably postoperative pain and tapentadol is administered
during $N_1$ consecutive days of a preferably postoperative phase $P_1$, optionally in combination with another analgesic,
during $N_2$ consecutive days of a phase $P_2$ directly following said preferably postoperative phase $P_1$, optionally in combination with another analgesic,
but not during $N_3$ consecutive days of a phase $P_3$ directly following said phase $P_2$;
wherein $N_1$, $N_2$ and $N_3$ are independently an integer of from 1 to 100, preferably with the proviso that $N_1 \geq N_2$.

When tapentadol is administered in combination with another analgesic, said another analgesic is preferably selected from the group of NSAIDs and opioids.

In a preferred embodiment, the daily dose of tapentadol that is administered during the $N_1$ consecutive days of the postoperative phase $P_1$ is identical with the daily dose of tapentadol that is administered during the $N_2$ consecutive days of a phase $P_2$ directly following said postoperative phase $P_1$.

In another preferred embodiment, the daily dose of tapentadol that is administered during the $N_1$ consecutive days of the postoperative phase $P_1$ is higher than the daily dose of tapentadol that is administered during the $N_2$ consecutive days of a phase $P_2$ directly following said postoperative phase $P_1$.

In still another preferred embodiment, the daily dose of tapentadol that is administered during the $N_1$ consecutive days of the postoperative phase $P_1$ is lower the daily dose of tapentadol that is administered during the $N_2$ consecutive days of a phase $P_2$ directly following said postoperative phase $P_1$.

In another preferred embodiment, the pain to be treated or the chronification of which to be inhibited is acute pain, preferably postoperative pain and tapentadol is administered
not during $N_1$ consecutive days of a preferably postoperative phase $P_1$,
but during $N_2$ consecutive days of a phase $P_2$ directly following said preferably postoperative phase $P_1$,
and not during $N_3$ consecutive days of a phase $P_3$ directly following said phase $P_2$;
wherein $N_1$, $N_2$ and $N_3$ are independently an integer of from 1 to 100, preferably with the proviso that $N_1 \geq N_2$.

Preferably, under these circumstances, another analgesic, preferably as defined above, is administered during the $N_1$ consecutive days of the postoperative phase $P_1$.

In still another preferred embodiment, the pain to be treated or the chronification of which to be inhibited is acute pain, preferably postoperative pain and tapentadol is administered
during $N_1$ consecutive days of a preferably postoperative phase $P_1$,
during $N_2$ consecutive days of a phase $P_2$ directly following said preferably postoperative phase $P_1$,
and during $N_3$ consecutive days of a phase $P_3$ directly following said phase $P_2$;
wherein $N_1$, $N_2$ and $N_3$ are independently an integer of from 1 to 100, preferably with the proviso that $N_1 \geq N_2$; and wherein the daily dose of tapentadol administered during the $N_3$ consecutive days of phase $P_3$ is below the analgesically effective daily dose of tapentadol, e.g. 25 mg.

In a preferred embodiment, when phase $P_1$ is "postoperative phase $P_1$", it is defined as the period of time after the surgery and in the post-anaesthetic care unit.

In another preferred embodiment, when phase $P_1$ is "postoperative phase $P_1$", it comprises the inflammatory phase and the proliferative phase of wound healing, but not the remodeling phase. In this regard, postoperative wound healing encompasses a complex series of events that begins at the moment of injury and can continue for months to years beginning with the inflammatory phase, followed by the proliferative phase, which in turn is followed by the remodeling phase. The inflammatory phase typically begins immediately after the injury/surgery and lasts 2-5 days and is characterized by hemostasis (vasoconstriction, platelet aggregation, clot formation of thromboplastin) as well as inflammation (vasodilation and phagocytosis). The proliferative phase typically takes place 2 days to 3 weeks and is characterized by granulation (fibroblasts lay bed of collagen, fill defect and produces new capillaries), contraction (wound edges pull together to reduce defect) and epithelialization (cross moist surface, cell travel about 3 cm from point of origin in all directions). Finally, the remodeling phase typically takes place 3 weeks to 2 years and is characterized by new collagen forms which increases tensile strength to wounds and scar tissue.

In a preferred embodiment, $N_3 \geq N_1 \geq N_2$. In another preferred embodiment, $N_3 \geq N_2 \geq N_1$.

Preferred embodiments $E^1$ to $E^{12}$ of phases $P_1$, $P_2$ and $P_3$ are summarized here below:

| days | $E^1$ | $E^2$ | $E^3$ | $E^4$ | $E^5$ | $E^6$ | $E^7$ | $E^8$ | $E^9$ | $E^{10}$ | $E^{11}$ | $E^{12}$ |
|---|---|---|---|---|---|---|---|---|---|---|---|---|
| $P_1/N_1$ | ≥1 | ≥1 | ≥2 | ≥2 | 2-7 | 2-7 | 2-5 | 2-5 | 2-5 | 2-5 | 2-5 | 2-5 |
| $P_2/N_2$ | ≤7 | ≤6 | ≤7 | ≤6 | 2-7 | 2-6 | 2-5 | 2-4 | 2-4 | 2-4 | 2-4 | 2-4 |
| $P_3/N_3$ | ≥2 | ≥4 | ≥6 | ≥8 | ≥10 | ≥12 | ≥14 | ≥16 | ≥18 | ≥20 | ≥22 | ≥24 |

Preferred embodiments $F^1$ to $F^{12}$ of phases $P_1$, $P_2$ and $P_3$ are summarized here below:

| days | $F^1$ | $F^2$ | $F^3$ | $F^4$ | $F^5$ | $F^6$ | $F^7$ | $F^8$ | $F^9$ | $F^{10}$ | $F^{11}$ | $F^{12}$ |
|---|---|---|---|---|---|---|---|---|---|---|---|---|
| $P_1/N_1$ | ≥1 | ≥1 | ≥2 | ≥2 | 2-7 | 2-7 | 2-5 | 2-5 | 2-5 | 2-5 | 2-5 | 2-5 |
| $P_2/N_2$ | ≤7 | ≤6 | ≤7 | ≤6 | 2-7 | 2-6 | 2-5 | 2-4 | 2-4 | 2-4 | 2-4 | 2-4 |
| $P_3/N_3$ | ≥2 | ≥4 | ≥6 | ≥8 | ≥10 | ≥12 | ≥14 | ≥16 | ≥18 | ≥20 | ≥22 | ≥24 |

Preferably, tapentadol is administered in form of a pharmaceutical composition containing besides tapentadol, additives and/or auxiliary substances.

Suitable additives and/or auxiliary substances in the context of this invention are all the substances known to the expert from the prior art for achieving galenical formulations. The choice of these auxiliary substances and the amounts thereof to be employed depend on whether the administration unit/dosage form is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration through the skin, are examples of suitable forms for percutaneous administration.

Examples of auxiliary substances and additives for the oral administration units/dosage forms are disintegrating agents, lubricants, binders, fillers, mold release agents, optionally solvents, flavorings, sugars, in particular carrier agents, diluents, dyestuffs, antioxidants etc. For suppositories, inter alia, waxes and fatty acid esters can be used, and for compositions for parental administration carrier substances, preservatives, suspension auxiliaries etc. can be used.

The dosage forms comprise preferably 0.05 wt.-% to 99.5 wt.-% of tapentadol, more preferably 0.1 to 90 wt.-%, still more preferably 0.5 to 80 wt.-%, most preferably 1.0 to 50 wt.-% and in particular 5.0 to 20 wt.-%.

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethyl cellulose, cellulose acetate, shellac, cetyl alcohol, polyvinylpyrrolidone, paraffins, waxes, naturally occurring and synthetic gums, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The administration units/dosage forms according to the invention may be controlled release, delayed release, prolonged release/extended release, sustained release, repeat-action release, etc. Prolonged release administration units/dosage forms are preferred.

The administration units/dosage forms according to the invention are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus, e.g., for a solid formulation, such as a tablet, tapentadol can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as e.g. water, in order to form a solid composition which comprises tapentadol in homogeneous distribution. Homogeneous distribution is understood here as meaning that tapentadol is uniformly distributed over the entire composition, so that this can easily be divided into unit dose forms, such as tablets, pills or capsules, having the same activity. The solid composition is then divided into unit dose forms. The administration units according to the invention can also be coated or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

Tapentadol can be released in a delayed or prolonged or sustained manner from administration units/dosage forms which can be used orally, rectally or percutaneously. Corresponding formulations, in particular in the form of a "twice daily (bid)" preparation which has to be taken only twice a day (bid), are particularly preferred for the indication according to the invention (cf. US-A-2005-58706).

Delayed or prolonged or sustained release of tapentadol may be achieved by administration units/dosage forms which contain tapentadol in a matrix, which contains e.g. 1 to 80% by weight, in particular 5 to 80 by weight, of one or more hydrophilic or hydrophobic polymers as pharmaceutically acceptable matrix forming agents and which comprise cellulose ethers and/or cellulose esters having a viscosity (determined using a Pharm. Eu. capillary viscosimeter) of 3,000 to 150,000 mPa s in a 2% by weight aqueous solution at 20° C. as pharmaceutically acceptable matrix forming agents. Preferred pharmaceutically acceptable matrix forming agents include polyethylene oxide having a molecular mass of more than 0.5 mio g/mol, cellulose ethers and/or cellulose esters having a viscosity between 10,000, in particular 50,000 mPa s, and 150,000 mPa s in a 2% by weight aqueous solution at 20° C. Particularly suitable pharmaceutically acceptable matrix forming agents may be selected from the group consisting of hydroxypropylmethyl celluloses (HPMC), hydroxyethyl celluloses, hydroxypropyl celluloses (HPC), methyl celluloses, ethyl celluloses and carboxymethyl celluloses and are selected, in particular, from the group consisting of HPMCs, hydroxyethyl celluloses and HPCs. HPMCs having a viscosity of approximately 100,000 mPa s, measured in a 2% by weight aqueous solution at 20° C. are most preferred.

The administration units/dosage forms according to the invention can exist both as a simple tablet and as a coated tablet, for example as a film tablet or dragee. The tablets are typically round and biconvex, but oblong tablet shapes which allow the tablet to be divided are also possible. Granules, spheroids, pellets or microcapsules which are poured into sachets or capsules or may be compressed to disintegrating tablets are also possible within the scope of the invention.

Instead of a slow release matrix, it is also possible to use a normal release matrix with a coating which retards release of the active ingredient. For example, tapentadol can be contained in a conventional matrix of microcrystalline cellulose and optionally further pharmaceutical auxiliaries such as binders, fillers, glidants, lubricants and flow regulators, which are covered or coated with a material controlling the slow release of tapentadol in an aqueous medium. Suitable coating agents include, for example, water-insoluble waxes and polymers such as polymethacrylates (Eudragit or the like) or water-insoluble celluloses, in particular ethyl cellulose. The coating material can optionally also contain water-soluble polymers such as polyvinyl pyrrolidone, water-soluble celluloses such as hydroxypropylmethyl cellulose or hydroxypropyl cellulose, other water-soluble agents such as Polysorbate 80 or hydrophilic pore-forming agents such as polyethylene glycol, lactose or mannitol.

As an alternative or a supplement to the possibilities of a slow release matrix in the delayed release or prolonged release or sustained release dosage forms or of a normal release matrix with a coating which retards the release of tapentadol, an osmotically driven release system can also be used to achieve a slow release. Embodiments and examples of the actual production of osmotically driven release systems can be found in U.S. Pat. Nos. 4,765,989, 4,783,337, and 4,612,008.

The following examples further illustrate the invention but are not to be construed as limiting its scope.

Example 1—Paw Incision Model for Postoperative Pain

Post operative, incisional pain is a common form of persistent, acute pain. Brennan et al. (Brennan T J, Vandermeulen E P, and Gebhart G F. Characterization of a rat model of incisional pain. Pain 1996; 64:493-501) developed a post operative model in rats with surgical intervention on the plantar surface of the hind foot for the evaluation of novel analgesic therapeutics. A surgical incision of the rat foot causes a reliable and quantifiable tactile hypersensitivity during the initial post operative period and lasting for several days after surgery. This model may thus be useful for predicting analgesia by investigational agents for post operative pain.

The experiments were carried out in male albino rats (Sprague Dawley) with 170 g-230 g body weight from a commercial breeder (Charles River, Germany). Surgery was performed as previously described. Brennan et al. (Brennan T J, Vandermeulen E P, and Gebhart G F. Characterization of a rat model of incisional pain. Pain 1996; 64:493-501). Briefly, rats were anaesthetised with isoflurane, and a 1 cm longitudinal incision was made, through skin and fascia of the plantar aspect of the foot, starting from the proximal edge of the heel and extending toward the metatarsal toes. The plantaris muscle was elevated and incised longitudinally. The muscle origin and insertion remained intact. After spreading of the muscle and haemostasis with gentle pressure, the skin was closed with two single interrupted sutures. After surgery, the rats were allowed to recover in their home cages and the animals regained consciousness within 2 to 5 minutes. In order to ensure a complete recovery from anaesthesia the baseline value of each individual animal was recorded not until 2 hours after surgery.

The rats were placed in a plastic cage with a wire mesh bottom which allowed full access to the paws. Hind paw withdrawal threshold after mechanical stimulation was tested with electronic von Frey hairs (Somedic Sales AB, Hörby, Sweden). Ten rats were used per experimental group. Animals were placed in a plastic cage with a wire mesh bottom which allowed full access to the paws. Behavioral accommodation was allowed for 30 min. In each case, withdrawal response was measured at an area adjacent to the wound (ipsilateral) and to the same area on the non-injured foot (contralateral). Two hours after surgery, primary hypersensitivity was tested as tactile withdrawal threshold (tactile hyperalgesia) shortly before drug administration and at different time points after drug application. Animals injected with vehicle served as controls. The pretest measurement was made prior to surgery and two thresholds were taken per test and averaged. Ten rats were used per experimental group. Tactile withdrawal threshold was measured pre and after substance administration from day 1 to day 5 post surgery. From day 6 to day 13 post surgery the withdrawal threshold was measured without substance administration (wash out phase). The efficacy was expressed as MPE %=% of maximal possible effect, whereas MPE is defined as 100% reversal of tactile hyperalgesia compared to vehicle group.

Tapentadol: Administration Dose/Route

Tapentadol at the dose of 14.7 mg/kg intraperitoneal route (i.p.) was adminstered twice daily (BID) (7 a.m./7 p.m.) throughout day 1 to day 5. The first administration was given 20 min before surgery on day 1. From day 6 to day 13 no substance was given (wash out phase) The study scheme is schematically illustrated in FIG. 1.

Results

Figure 2:
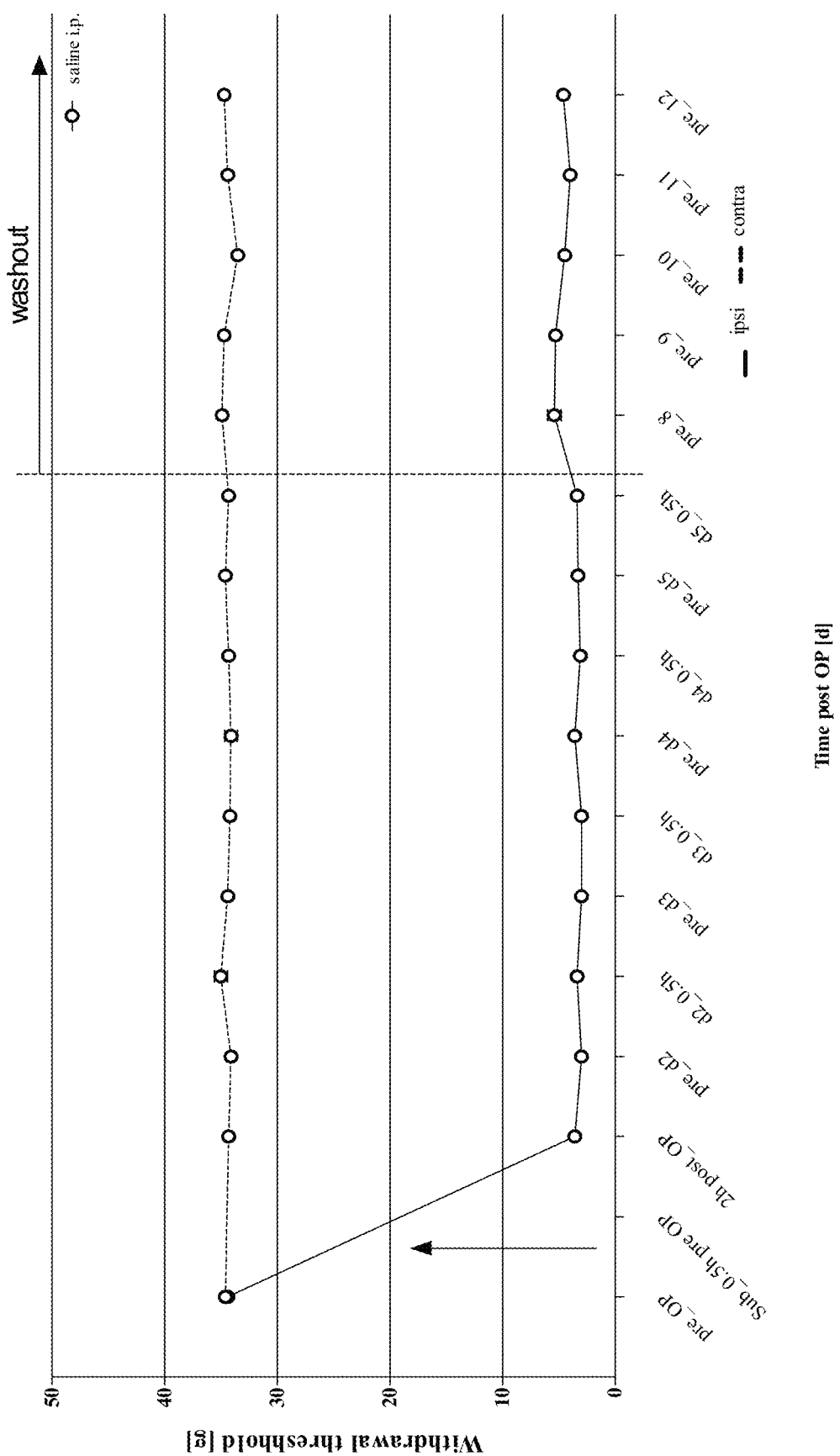
FIG. 2 shows the results for sustained tactile hypersensitivity following surgical lesion outlasts treatment duration (i.e. still present in washout phase)

As evidenced by FIG. 2, increased sensitivity to tactile stimuli (decreased withdrawal threshold to stimulation with von Frey hair, so-called tactile hyperalgesia) starts shortly after paw incision and lasts until the end of the study (for at least 12 days post surgery).

Figure 3:
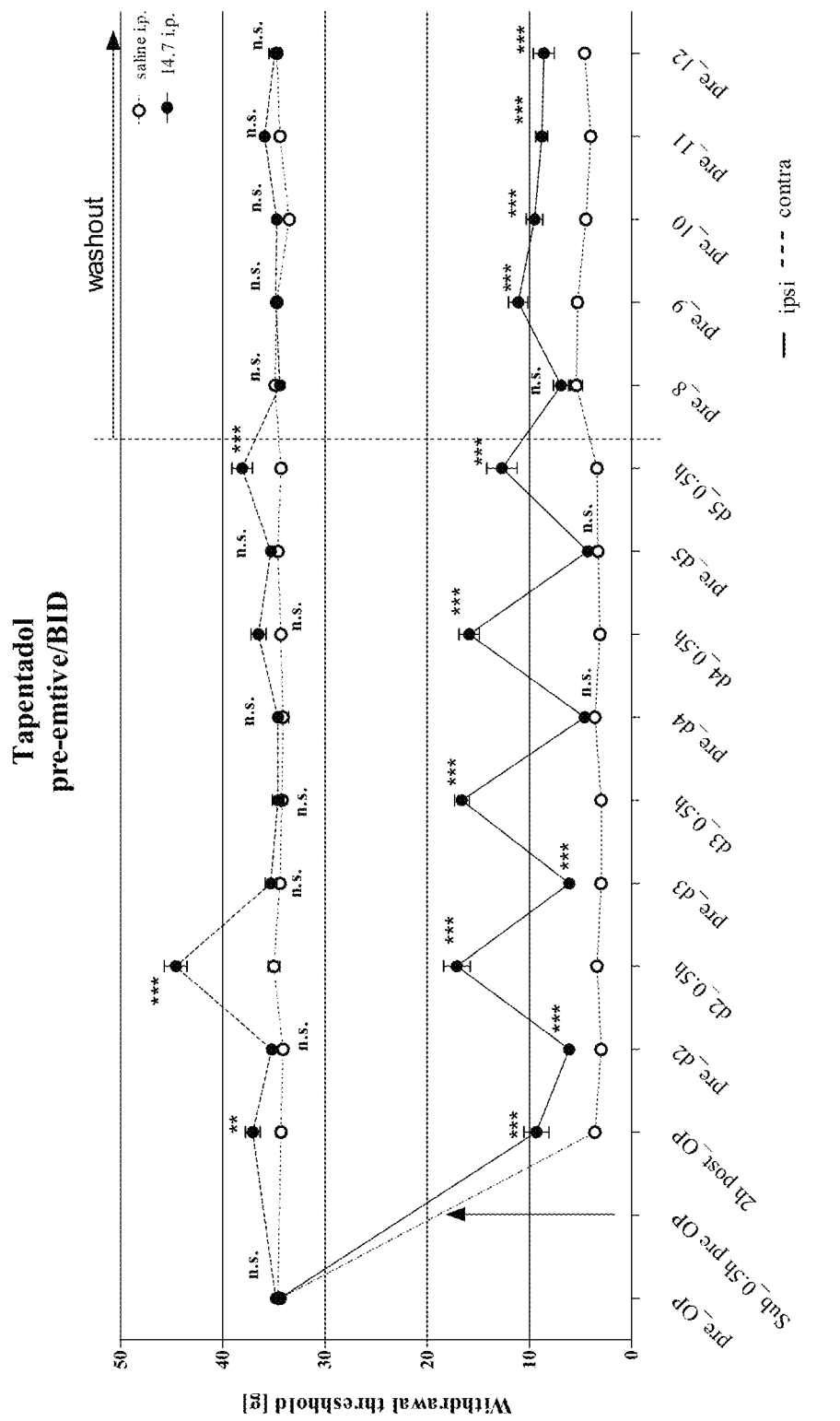
FIG. 3 shows the effect of tapentadol on withdrawal thresholds after tactile stimulation of injured hindpaw (ipsi) and not injured hindpaw (contra) in the paw incision model of postoperative pain. N=10 animals per group. *=$p<0.001$; =$p<0.01$; *=$p<0.05$, n.s.=not significant.

The effect of tapentadol on sustained tactile hyperalgesia following surgical lesion outlasts treatment duration (i.e. still present in washout phase) (FIG. 3; Table 1).

Intraperitoneal administration of Tapentadol at the dose of 14.7 mg/kg (BID) showed an effect of 38.3±5.48% (reduction of tactile hyperalgesia) compared to the saline group; (FIG. 3; Table 1).

After 5 days of BID intraperitoneal treatment the efficacy was 22.8±5.29% (last day of treatment) (FIG. 3; Table 1).

Figure 4:
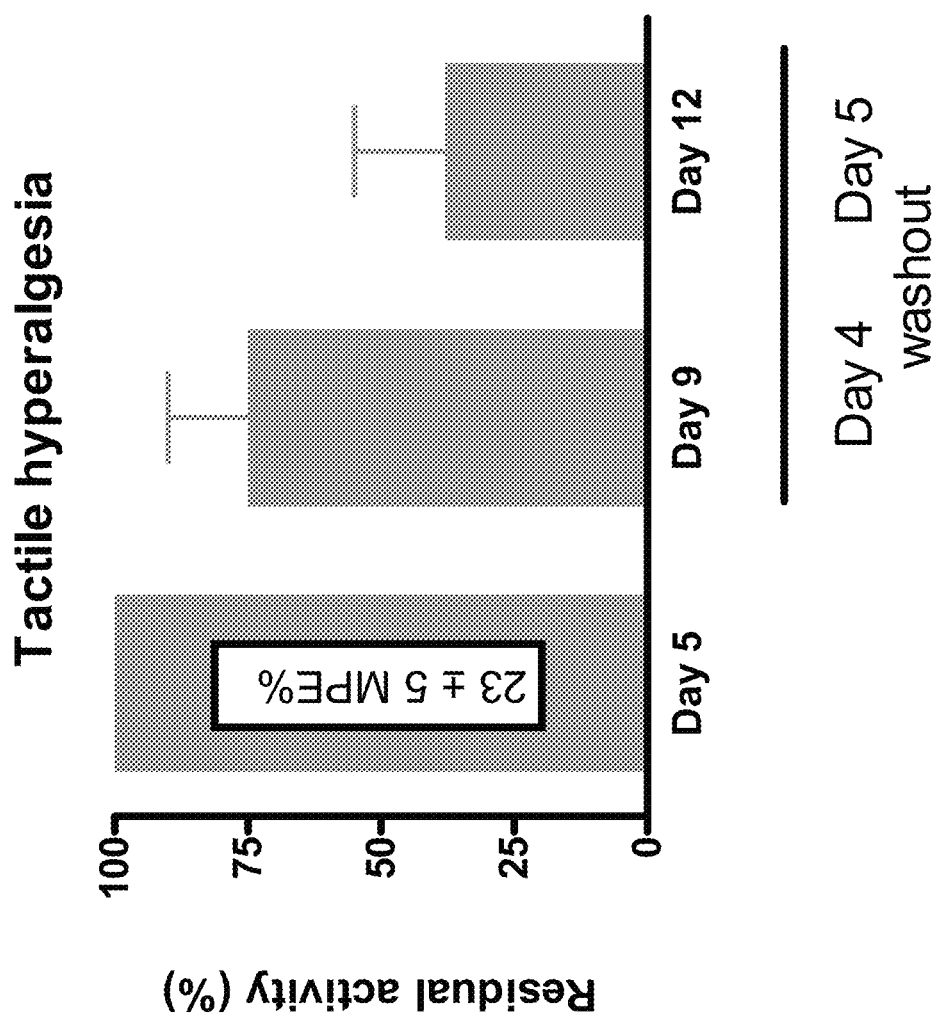
FIG. 4 shows the remaining efficacy of tapentadol in the washout phase compared to the effect on the last treatment day (day 5).

On the third day of washout (day 8) the remaining efficacy was 3%, and increased on the following day (day 9) to 17% (FIG. 3; Table 1). This remaining efficacy was 74% of the efficacy after substance treatment on day 5 (FIG. 4). After 7 days of washout the remaining efficacy was 9%, which represented 39% of the efficacy after substance treatment on day 5 (FIG. 4).

TABLE 1

Effect of Tapentadol on tactile hyperalgesia in the paw incision model for postopertative pain

| group | dose [mg/kg] | MPE % time [day] | | |
|---|---|---|---|---|
| | | d 2_0.5 h | pre-d 3 | d 3-0.5 h |
| vehicle | 14.7 | 1.20 ± 0.75 | 0.00 ± 0.32 | 0.0 ± 0.49 |
| Tapentadol | | 38.3 ± 4.58 *** | −0.6 ± 2.21 n.s. | 36.8 ± 2.41 *** |
| | dose [mg/kg] | pre-d 4 | d 4-0.5 h | pre-d 5 |
| | 14.7 | 1.90 ± 0.68 | 0.30 ± 0.63 | 0.90 ± 0.82 |
| | | −6.00 ± 1.63 ** | 34.5 ± 3.27 *** | −6.60 ± 1.67 ** |
| | dose [mg/kg] | d 5-0.5 h | pre-d 8 | pre_d 9 |
| | 14.7 | 1.10 ± 0.59 | 7.70 ± 1.96 | 7.20 ± 1.26 |
| | | 22.8 ± 5.29 *** | 2.60 ± 2.51 n.s. | 17.2 ± 3.43 ** |
| | dose [mg/kg] | pre-d 10 | pre-d 11 | pre_d 12 |
| | 14.7 | 4.80 ± 0.82 | 3.00 ± 1.22 | 5.00 ± 1.30 |
| | | 11.4 ± 3.21 *** | 8.90 ± 2.59 *** | 8.60 ± 3.94 *** |

MPE % = % of maximal possible effect; MPE is defined as 100% reversal of tactile hyperalgesia compared to vehicle group; pre = pre substance administration or effect without treatment; pre-d 8 to pre d-9 = effect in washout phase; d 2_0.5 h = effect at 0.5 h after substance treatment on day two after surgery; no analysis on the day of surgery (day 1); similar abbreviations for the other days
[N = 10 animals per group.
*** = $p < 0.001$;
** = $p < 0.01$;
* = $p < 0.05$,
n.s. = not significant.]

Example 2—Respective Effects of Tapentadol on Mechanical Allodynia/Hyperalgesia in Rats with Ligatures of the Infraorbital Nerve Versus the Sciatic Nerve Methods Male Sprague-Dawley rats (Charles River Laboratories, L'Arbresle, France), weighing 150-200 g on arrival, were used. Animals were maintained under controlled environmental conditions (22±1° C., 60% relative humidity, 12 h/12 h light/dark cycle, food and water ad libitum) starting from reception in the laboratory, for at least 1 week before any intervention or treatment and thereafter, until euthanasia.

Chronic Constriction Injury to the Infraorbital Nerve (CCI-ION)

Rats were anaesthetized with sodium pentobarbital (50 mg/kg i.p.). Unilateral CCI-ION was performed under direct visual control using a Zeiss microscope (10-25×). Briefly, the head was fixed in a Horsley-Clarke stereotaxic frame and a midline scalp incision was made, exposing skull and nasal bone. The edge of the orbit, formed by the maxillary, frontal, lacrimal, and zygomatic bones, was dissected free. The orbital contents were then gently deflected to give access to the infraorbital nerve which was dissected free at its most rostral extent in the orbital cavity, just caudal to the infraorbital foramen. Only 5 mm of the nerve could be freed, providing the space for placement of two chromic catgut (5-0) ligations tied loosely (with about 2 mm spacing) around it. To obtain the desired degree of constriction, the criterion formulated by Bennett and Xie (1988) was used: the ligations reduced the diameter of the nerve by a just noticeable amount and retarded, but did not interrupt, epineurial circulation. Finally, scalp incision was closed using silk sutures (4-0). In sham-operated rats, the ION was exposed using the same procedure, but was not ligated.

Chronic Constriction Injury to the Sciatic Nerve (CCI-SN)

Rats were anaesthetized as above and the common sciatic nerve was exposed. Using a dissection microscope (2× magnification), four chromic catgut (5-0) ligations were tied loosely with about 1 mm spacing, proximally to the sciatic trifurcation (Bennett and Xie, 1988). Finally, the skin and muscle were sewed using silk sutures (4-0). In sham-operated animals, the same surgery was performed, but the nerve was not ligated.

For both CCI-ION and CCI-SN surgeries, rats were gently put on a warming pad until recovery from anaesthesia and then returned to their home cages (3 animals per cage of 42×42×18 cm).

Pharmacological Treatments

Tapentadol (1, 3 and 10 mg/kg i.p.), reboxetine (10 mg/kg i.p.), morphine (1 and 3 mg/kg s.c.) or their vehicle (0.9% NaCl) were injected acutely 14 days after surgery, when allodynia/hyperalgesia reached a plateau in both CCI-SN and CCI-ION rats. Behavioral tests were performed at various times for up to 4 h after injection. In drug association procedure, reboxetine or saline was administered 15 min before morphine or saline.

Subchronic treatment consisted of twice daily injections of tapentadol (10 mg/kg, i.p. at 10:00 am and 6:00 pm) or saline for 4 days starting on the $15^{th}$ day after nerve ligation in both CCI-ION and CCI-SN rats. Animals were further injected with tapentadol (10 mg/kg i.p.) or saline at 10:00 am the following day ($19^{th}$ day post-surgery), and assessment of allodynia with von Frey filament tests (see below) was made at various times up to 4 hours after this injection. All rats were killed by decapitation 4 hours after the last injection for real-time qRT-PCR determinations of specific mRNAs in ganglia and central tissues (see below).

Behavioral Testing

Von Frey Filaments in CCI-ION Rats

Rats were placed individually in small (35×20×15 cm) plastic cages for a 2 h habituation period. Before any stimulation session, rats freely explored the observation cage and the testing environments for 2 h. Then mechanical sensitivity was determined with a graded series of eleven von Frey filaments (Bioseb, Bordeaux, France). The filaments produced a bending force of 0.40, 0.60, 1.00, 2.00, 4.00, 6.00, 8.00, 10.00 and 12.00 g, respectively. The stimuli were applied within the ION territory (vibrissae pad) three times on the nerve-injured side and then on the contralateral side for a total of 6 applications of each filament per rat, always beginning with the filament producing the lowest force. The von Frey filaments were applied at least 3 seconds after the rat had returned to its initial resting state. For each session, the complete series of von Frey filaments was tested in increasing force order. Behavioral nociceptive response consisted of either (1) a brisk withdrawal reaction: the rat pulled briskly backward; (2) an escape/attack: the rat avoided further contact with the filament either passively by moving its body away from the stimulating object to assume a crouching position against cage wall, sometimes with the head buried under the body, or actively by attacking the stimulating object, making biting and grabbing movements; or (3) asymmetric face grooming: the rat displayed an uninterrupted series of at least 3 face-wash strokes directed to the stimulated facial area, often preceded by the brisk withdrawal reaction. The latter responses represented the highest scores in the rank-ordered response scoring system initially described by Vos et al. (1994). Under our own conditions, the mechanical response threshold was determined as the minimal force filament causing at least one among these responses to at least 2 out of the 3 applications in vibrissae territory. The 12.00 g filament was the cut-off threshold (no tissue-injury occurred with this pressing force). In the preoperative tests, stimulation with the 12.00 g filament did not induce any nociceptive behavior in the majority of the rats (>90%). To avoid nonspecific responses, only these rats were included in the study.

Von Frey Filaments in CCI-SN Rats

Before testing, each rat was habituated for 2 h as above, and mechanical sensitivity was then determined with a graded series of eight von Frey filaments, that produced a bending force of 6, 8, 10, 12, 15, 26, and 60 g, respectively. The stimuli were applied within the SN territory (lateral part of the hind paw sole). Each filament was tested three times on the nerve-injured side in increasing order starting with the filament producing the lowest force. As for the CCI-ION rats, the von Frey filaments were applied at least 3 seconds after the rat had returned to its initial resting state. The minimal force filament for which animals presented either a brisk paw withdrawal and/or an escape attempt in response to at least 2 out of the 3 stimulations allowed determination of the mechanical response threshold. The 60.00 g filament was chosen as the cutoff threshold to inhibit any tissue injury.

Paw Pressure Test in CCI-SN Rats

Nociceptive thresholds, expressed as g, were measured by applying increasing pressure to the nerve-injured hindpaw using an Ugo Basile analgesimeter (Bioseb, Chaville, France). The responses used to quantify the nociceptive thresholds were the hindpaw withdrawal and the vocalization of the animals (Randall and Selitto, 1957). Increasing pressure was applied to the nerve-injured hindpaw until hindpaw withdrawal and then a squeak (i.e. the vocalization threshold when the paw was held under pressure) were obtained. As hindpaw withdrawal is a spinally coordinated reflex whereas vocalization is a supra-spinal integrated response, this test provides a preliminary assessment of the respective contribution of spinal versus supra-spinal mechanisms.

Tissue Collection and RNA Extraction

Animals used for qRT-PCR procedure were decapitated immediately after performance of von Frey filament test four hours after the last injection of tapentadol or saline for subchronic treatment conditions (see above). Trigeminal ganglia and spinal nucleus pars caudalis (Sp5c) for CCI-ION rats and L4-L5 dorsal root ganglia (DRG) and the ipsi- and contra-lateral dorsal quadrants of the lumbar enlargement of the spinal cord for SN-CCI rats were dissected at 0-4° C., and tissues were immediately frozen in liquid nitrogen and stored at −80° C. For total RNA extraction, the NucleoSpin RNA II extraction kit (Macherey-Nagel, Hoerdt, France) was used.

Real Time qRT-PCR

First-stranded cDNA synthesis (from 660 ng total RNA per 20 µl reaction mixture) was carried out using SuperScript™ III Reverse Transcriptase and random primers (250 ng per reaction), as recommended by the manufacturer (Invitrogen, Cergy Pontoise, France). PCR amplification, in triplicate for each sample, was then performed using ABI Prism 7300 (Applied Biosystems, Courtaboeuf, France), ABgene® ABsolute QPCR ROX Mix (ABgene, Couraboeuf, France) and Assays-on-Demand Gene Expression probes (Applied Biosystems) for target genes: Activating Transcription Factor 3 (ATF3; Rn00563784_m1), interleukin-6 (IL6; Rn00561420_m1) and Brain Derived Neurotrophic Factor (BDNF, Rn02531967_s1). Semi-quantitative determinations were made with reference to the reporter gene encoding glyceraldehyde 3-phosphate dehydrogenase (GaPDH; Rn99999916_s1). The reaction started with the polymerase activation step at 95° C. for 15 min and proceeded with 30-40 cycles of 15 s at 95° C. and 60 s at 60° C. The validity of the results was regularly checked by running appropriate negative controls (replacement of cDNA by water for PCR amplification; omission of reverse transcriptase for cDNA synthesis). Specific mRNA levels were calculated after normalizing from GaDPH mRNA in each sample (Latrémolière et al., 2008). Data are presented as relative mRNA units compared to control values.

Statistical Analyses

Results are expressed as the means±S.E.M. Repeated measures' analysis of variance (ANOVA) followed by Dunnett's test was conducted to compare drugs effects over time. One way ANOVA followed by Newman-Keuls test was used to compare drugs effects on mRNA levels. Areas under the time-course curves (AUC) were calculated using the trapezoidal rule. Statistical significance of differences in AUC values corresponding to various treatment groups was analyzed by the Student's t test. The significance level was set at $P<0.05$.

Results

Effects of Acute or Subchronic Treatment with Tapentadol in CCI-SN Rats

Randall-Selitto Test

Figure 5:
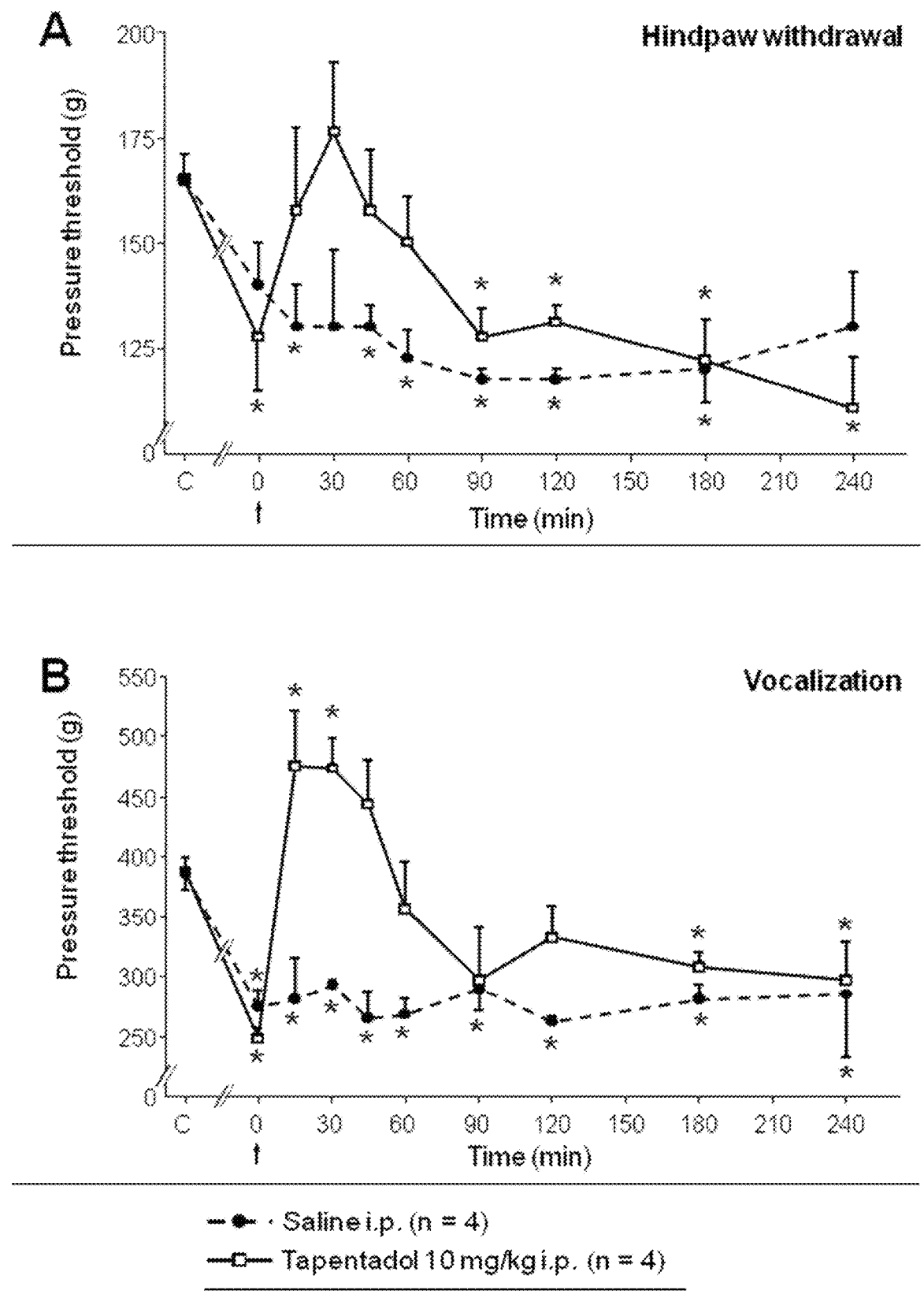
FIG. 5 illustrates the anti-hyperalgesic effects of tapentadol in CCI-SN rats.

FIG. 5: Anti-Hyperalgesic Effects of Tapentadol in CCI-SN Rats.

Tapentadol (10 mg/kg i.p.) or saline was injected (0 on abscissa) two weeks after unilateral chronic constriction injury to the sciatic nerve, and the Randall-Selitto test was used to determine pressure threshold values (as g) to trigger hindpaw withdrawal (A) and vocalization (B) at various times thereafter. Each point is the mean±S.E.M. of 4 independent determinations. * P<0.05, compared to pressure threshold values in control healthy rats (before surgery, C on abscissa), Dunnett's test.

Pressure threshold values to evoke withdrawal of hindpaw ipsilateral to CCI-SN (FIG. 5A) and vocalization (FIG. 5B) were significantly decreased two weeks after unilateral ligation of the sciatic nerve. At this time, acute i.p. administration of saline did not significantly affect CCI-SN-induced decreases in both pressure threshold values (FIGS. 5A,B). In contrast, tapentadol, at the dose of 10 mg/kg i.p., produced a rapid increase in these values, which lasted for at least 60 min after the drug administration. Indeed, for the first hour after tapentadol treatment, pressure threshold values to cause hindpaw withdrawal did not significantly differ from those determined in intact healthy rats, before surgery for nerve ligations (FIG. 5A). Regarding vocalization, pressure threshold values to trigger this response were even slightly higher (+20%) for the first 45 min after tapentadol administration in CCI-SN rats than in untreated healthy rats (FIG. 5B), suggesting the occurrence of an analgesic effect in addition to reversal of CCI-SN-induced hyperalgesia.

Von Frey Filaments Test

Figure 6:
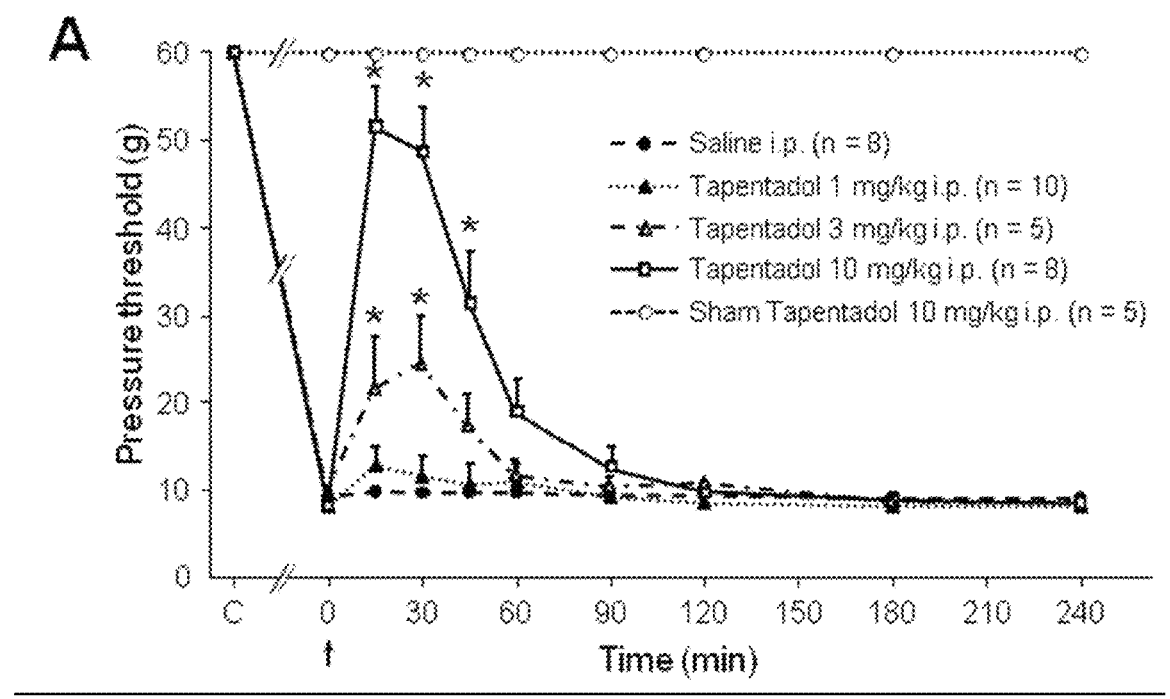
FIG. 6 shows the anti-allodynic effects of acute or subchronic treatment with tapentadol in CCI-SN rats.
Figure 6:
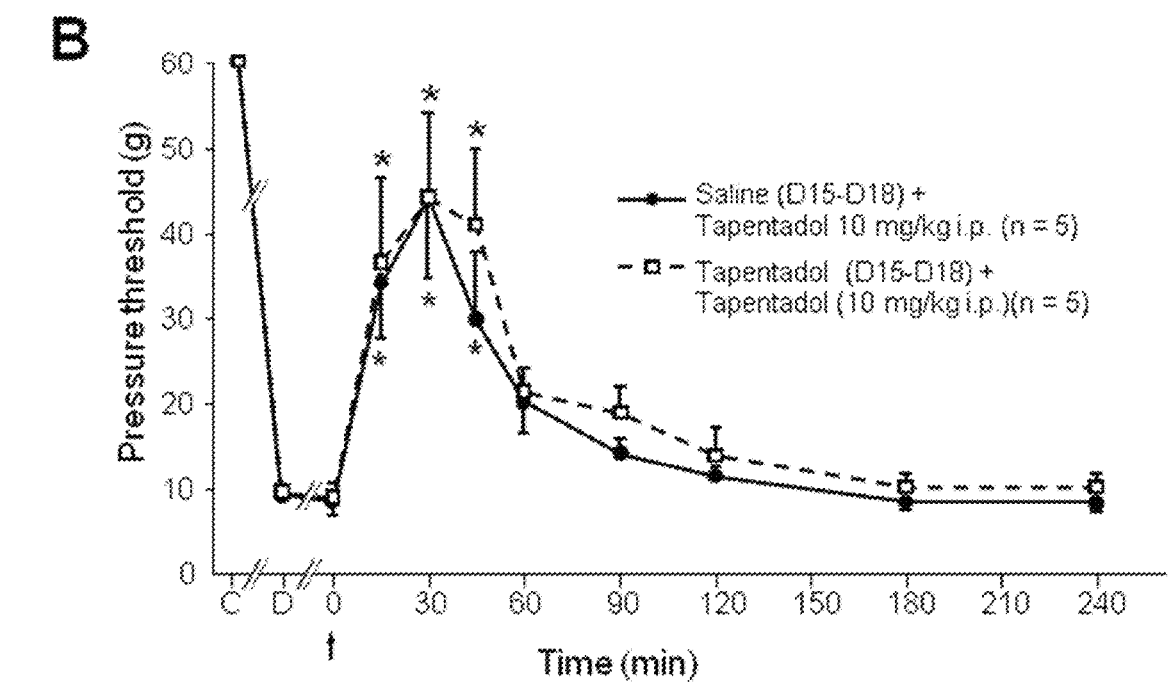

FIG. 6: Anti-Allodynic Effects of Acute or Subchronic Treatment with Tapentadol in CCI-SN Rats.

A—Two weeks after unilateral chronic constriction injury to the sciatic nerve, pressure threshold values (as g) to trigger nocifensive responses to von Frey filaments application onto the plantar surface of ipsilateral hindpaw were determined at various times after acute injection of tapentadol (1, 3 or 10 mg/kg, i.p.) or saline. B—On day 15 (D on abscissa) after nerve ligation, rats were treated subchronically with tapentadol (10 mg/kg, i.p., twice daily, at 10:00 AM and 6:00 PM) or saline for four days. On the following day (day 19 after surgery), both tapentadol- and saline-pretreated CCI-SN rats were injected with tapentadol (10 mg/kg, i.p.; 0 on abscissa) and then subjected to von Frey filaments' test applied to ipsilateral hindpaw for determination of pressure threshold values (as g) at various times thereafter. Each point is the mean±S.E.M. of 5-10 independent determinations. * P<0.05, compared to pressure threshold values determined just prior to tapentadol or saline injection, Dunnett's test.

On abscissa: C, intact healthy rats before surgery; D, day 15 after unilateral ligation of the sciatic nerve; 0, injection of tapentadol or saline on day 15 (A) or day 19 (B) after SN-CCI.

As depicted in FIG. 6, pressure threshold to trigger hindpaw withdrawal in response to plantar application of von Frey filaments on the ligated side was lowered by 85% in CCI-SN rats compared to intact healthy rats. At the dose of 1 mg/kg i.p., tapentadol exerted a discrete effect only, resulting in an approximately 40% (non significant) increase in pressure threshold value for the first 15-30 min after injection (FIG. 6A). In contrast, a huge effect was noted after the administration of 10 mg/kg i.p. of tapentadol since pressure threshold values no longer differed from healthy control values in CCI-SN rats at 15-30 min after the drug administration (FIG. 6A). Thereafter, the effect of tapentadol progressively vanished, and 90 min after the drug injection, mechanical allodynia did not significantly differ from that measured in saline-treated CCI-SN rats. At the dose of 3 mg/kg i.p., tapentadol also increased pressure threshold values, but to a lower extent than 10 mg/kg i.p., indicating a clear dose-dependent anti-allodynic effect of the drug in the 1-10 mg/kg i.p. dose range in CCI-SN rats (FIG. 6A).

In order to assess the possible occurrence of sensitization/desensitization to tapentadol under subchronic treatment conditions, a second series of experiments consisted of comparing the effects of repeated versus acute treatment with the drug. The data in FIG. 6B show that tapentadol administration produced the same anti-allodynic effects whether CCI-SN rats had been pretreated for the four preceding days with saline or tapentadol. As after acute treatment in the previous series of experiments (FIG. 6A), tapentadol markedly increased pressure threshold values for the first 45 min after injection, and this effect progressively disappeared following similar time course whether or not CCI-SN rats had been pretreated with the drug (FIG. 6B).

Effects of Acute or Subchronic Treatment with Tapentadol in CCI-ION Rats

Von Frey Filaments Test

Figure 7:
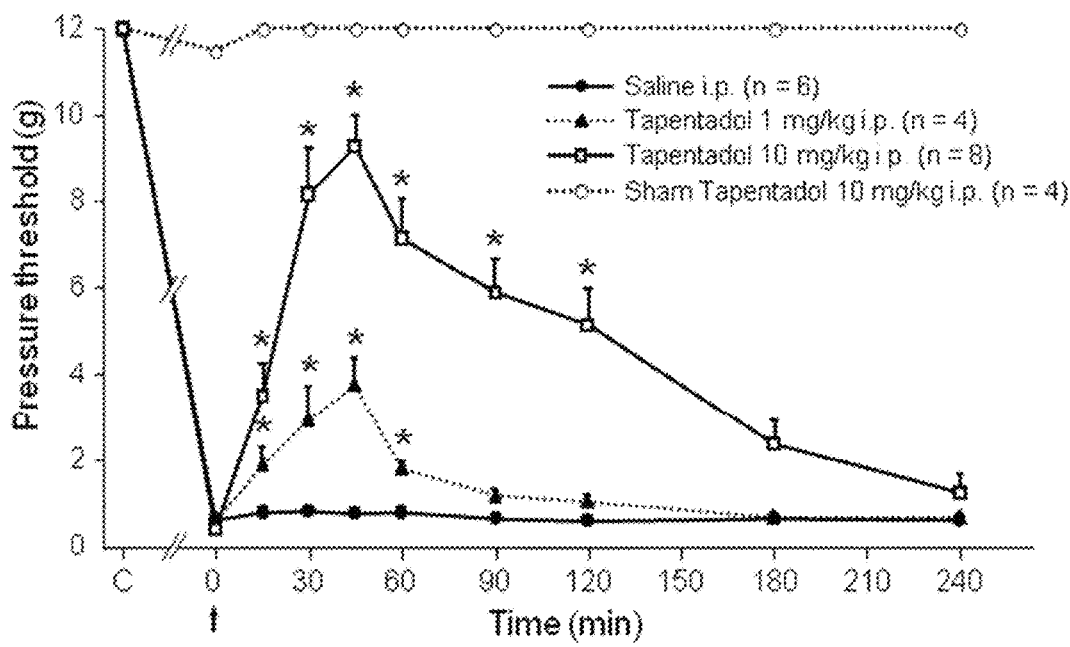
FIG. 7 illustrates the anti-allodynic effects of acute or subchronic treatment with tapentadol in CCI-ION rats.
Figure 7:
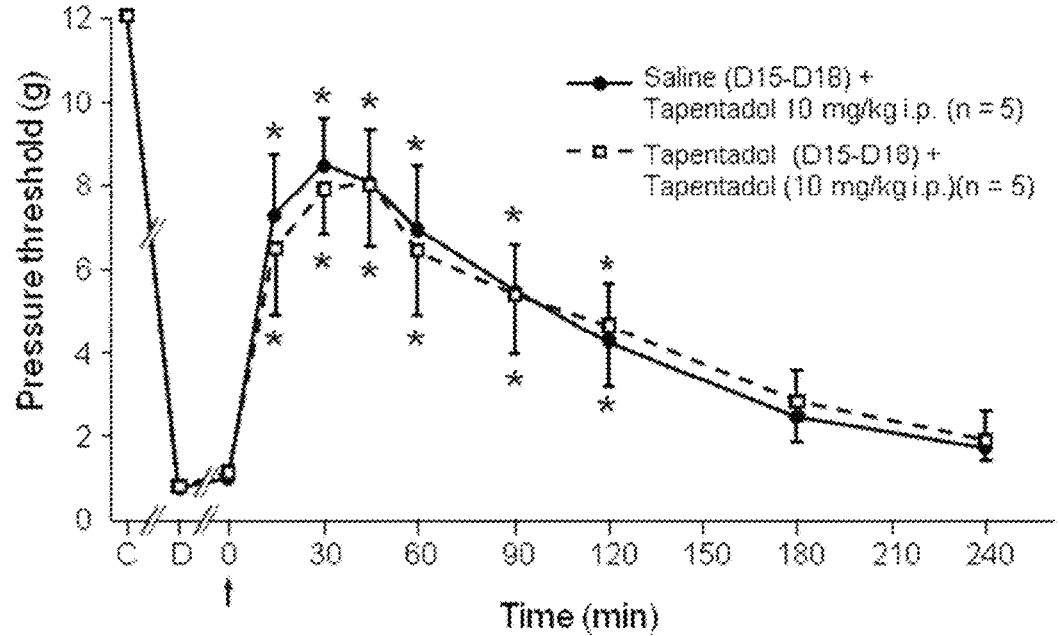

FIG. 7: Anti-Allodynic Effects of Acute or Subchronic Treatment with Tapentadol in CCI-ION Rats.

A—Two weeks after unilateral chronic constriction injury to the infraorbital nerve, pressure threshold values (as g) to trigger nocifensive responses to von Frey filaments application onto ipsilateral vibrissal pad were determined at various times after acute injection of tapentadol (1 or 10 mg/kg i.p.) or saline. B—On day 15 (D on abscissa) after nerve ligation, rats were treated subchronically with tapentadol (10 mg/kg, twice daily, at 10:00 AM and 6:00 PM) or saline for four days. On the following day (day 19 after surgery), both tapentadol- and saline-pretreated CCI-ION rats were injected with tapentadol (10 mg/kg i.p.; 0 on abscissa) and then subjected to von Frey filaments' test applied to ipsilateral vibrissal pad for determination of pressure threshold values at various times thereafter. Each point is the mean±S.E.M. of 4-8 independent determinations. * P<0.05, compared to pressure threshold values determined just prior to tapentadol or saline injection, Dunnett's test.

On abscissa: C, intact healthy rats before surgery; D, day 15 after unilateral ligation of the infraorbital nerve; 0, injection of tapentadol or saline on day 15 (A) or day 19 (B) after CCI-ION.

A marked mechanical allodynia was observed two weeks after unilateral CCI to the infraorbital nerve. As shown in FIG. 7A, pressure threshold value to trigger nocifensive response to the application of von Frey filaments onto vibrissal pad in CCI-ION rats was less than 5% of that determined in intact healthy rats. Acute i.p. administration of tapentadol at 1 mg/kg i.p. produced an up to 6-fold increase in pressure threshold value compared to that determined in saline-treated CCI-ION rats. This increase developed progressively for the first 45 min after tapentadol injection, then pressure threshold values returned, within the following 45 min, down to the same bottom level as that found in saline-treated CCI-ION rats (FIG. 7A). At the dose of 10 mg/kg i.p., the anti-allodynic effect of tapentadol was markedly larger in both amplitude and duration since 30-60 min after the drug injection, pressure threshold values were up to 15-20-fold higher than those determined prior to injection. Furthermore, at this dose, the anti-allodynic effect of tapentadol assessed through drug-induced increase in pressure threshold values remained statistically significant for at least two hours after the drug injection (FIG. 7A).

In a second series of experiments, the same protocol as that used above for subchronic treatment in CCI-SN rats was applied to CCI-ION rats. It was noted that the anti-allodynic effect of tapentadol (10 mg/kg i.p.) had the same characteristics (amplitude, duration) whether CCI-ION rats had received repeated injections of saline or tapentadol for the four preceding days (FIG. 7B). Therefore, neither in CCI-SN rats nor in those with CCI-ION, any sign of sensitization or desensitization to tapentadol under subchronic treatment conditions could be detected.

Effects of Morphine and Reboxetine, Alone or Combined, in Nerve-Ligated Rats

In CCI-SN Rats

Figure 8:
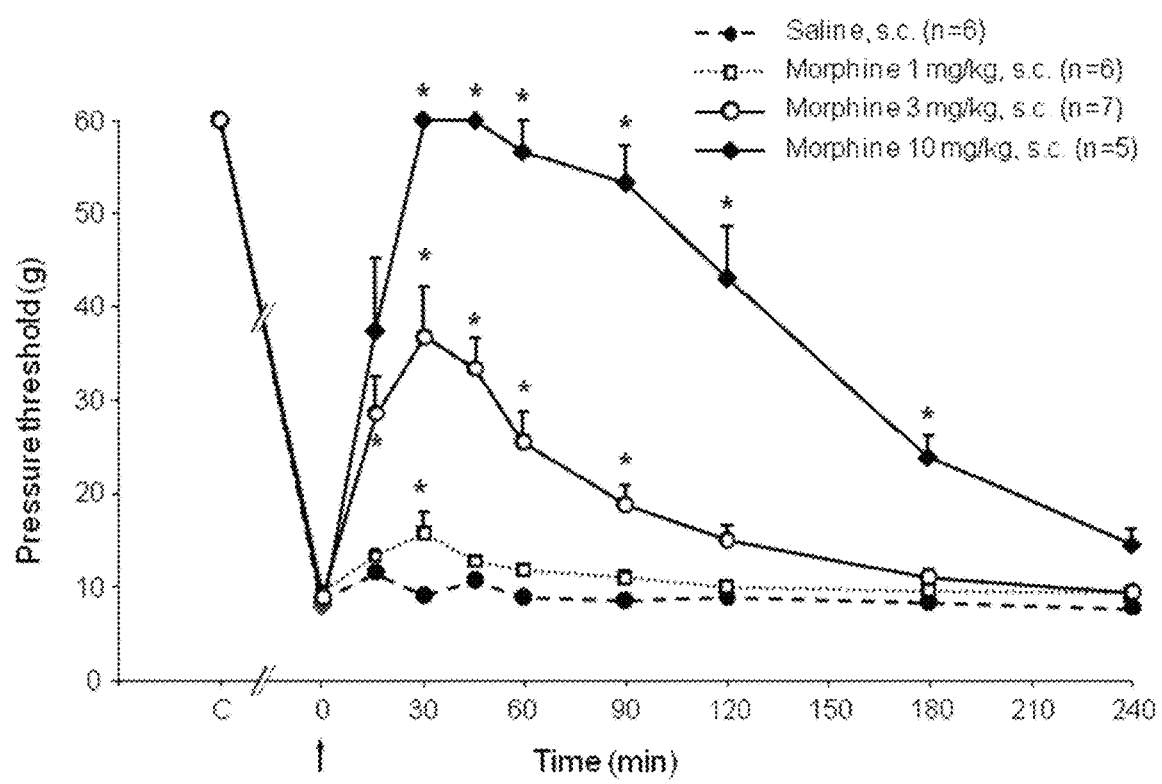
FIG. 8 shows the dose-dependent anti-allodynic effects of morphine in CCI-SN rats

FIG. 8: Dose-Dependent Anti-Allodynic Effects of Morphine in CCI-SN Rats

Two weeks after unilateral chronic constriction injury to the sciatic nerve, pressure threshold values (as g) to trigger nocifensive responses to von Frey filaments application onto the plantar surface of ipsilateral hindpaw were determined at various times after acute injection (0 on abscissa) of morphine (1, 3 or 10 mg/kg s.c.) or saline. Each point is the mean±S.E.M. of 5-7 independent determinations. * $P<0.05$, compared to pressure threshold values determined just prior to morphine or saline injection, Dunnett's test.

C on Abscissa, Intact Healthy Rats Before Surgery.

Before performance of these experiments, it was first determined the dose-dependent effect of acute treatment with morphine on mechanical allodynia in CCI-SN rats. As shown in FIG. 8, morphine at the dose of 10 mg/kg s.c. fully reversed CCI-SN-induced mechanical allodynia as soon as 30 min after the drug injection, and this effect persisted for at least one hour. A the other two doses tested, 1 and 3 mg/kg s.c., allodynia was not completely reversed by morphine and the drug effect was of shorter duration (FIG. 4). This led us to select these latter two doses for investigating whether or not reboxetine could interact with the effect of morphine.

Figure 9:
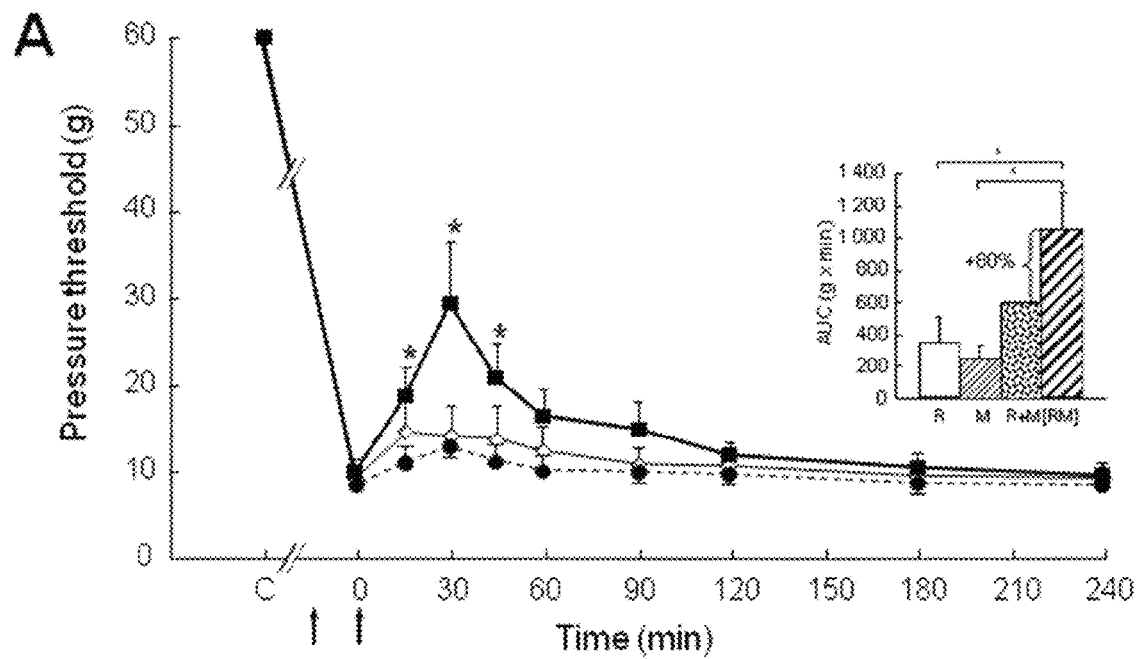
FIG. 9 illustrates the anti-allodynic effects of acute administration of reboxetine and morphine, alone or combined, in CCI-SN rats.
Figure 9:
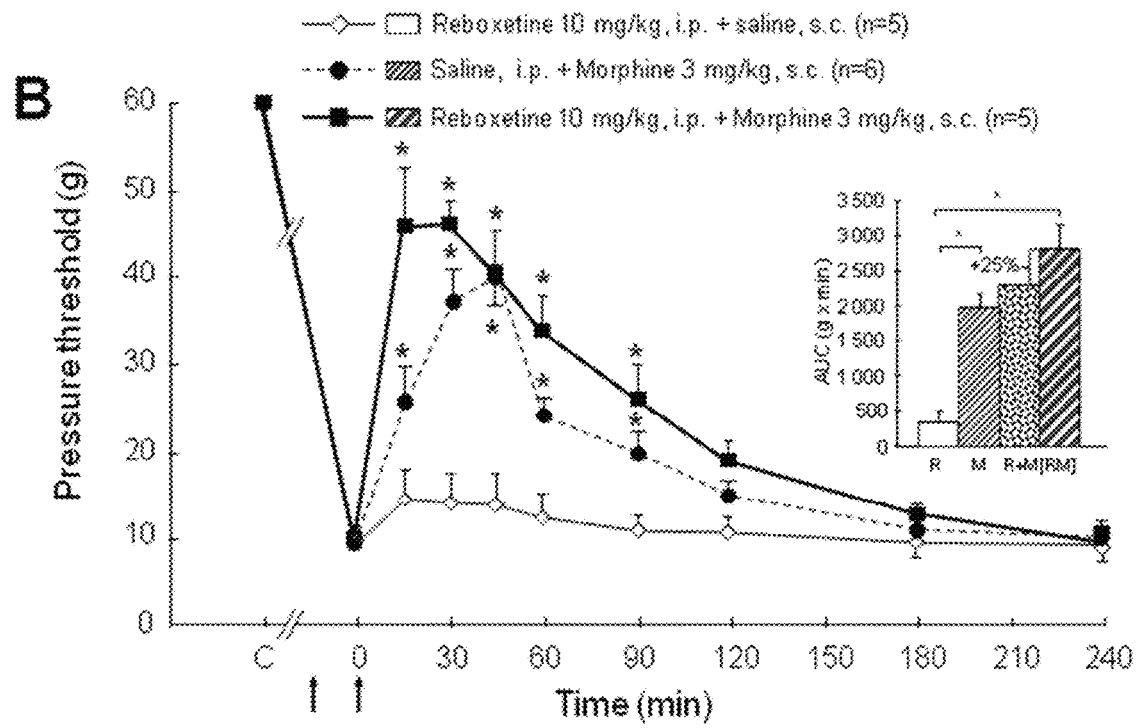

FIG. 9: Anti-Allodynic Effects of Acute Administration of Reboxetine and Morphine, Alone or Combined, in CCI-SN Rats.

Two weeks after unilateral chronic constriction injury to the sciatic nerve nerve, pressure threshold values (as g) to trigger nocifensive responses to von Frey filaments application onto the plantar surface of ipsilateral hindpaw were determined at various times after injection of reboxetine (10 mg/kg i.p.) or saline, followed 15 min later by injection of morphine at 1 mg/kg s.c. (A) or 3 mg/kg s.c. (B) or saline. Each point is the mean±S.E.M. of 5-6 independent determinations.

* $P<0.05$, compared to pressure threshold values determined in CCI-SN rats just prior to the second injection ($2^{nd}$ arrow, 0 on abscissa), Dunnett's test.

Bar diagrams: AUC values calculated from the respective time-course curves: R=reboxetine+saline; M=saline+morphine; [RM]=reboxetine+morphine. The third bar, R+M, corresponds to the sum of the first two bars, R and M.

* $P<0.05$, Student's t test.

In a first series of drugs combination experiments, CCI-SN rats were injected with reboxetine (10 mg/kg i.p.) or saline then morphine (1.0 mg/kg s.c.) or saline 15 min later, and animals were subjected to von Frey filaments test for the following 4 hours. As shown in FIG. 9A, only discrete increases in pressure threshold values were noted after the administration of either drug alone. In contrast, a significant increase was noted after the combined treatment indicating a clear-cut antiallodynic effect of reboxetine+morphine in CCI-SN rats (FIG. 9A). Calculation of respective AUC values yielded for the reboxetine+morphine combination [RM] a value 80% higher than the sum R+M of the respective values for reboxetine or morphine administered alone (FIG. 9A), indicating that the resulting antiallodynic effect of the drug combination largely exceeded that expected from simple addition of the effects of each drug considered separately.

Whether such an apparent synergy between reboxetine and morphine may also occur at the intermediate dose of the opiate drug, 3.0 mg/kg s.c., was tested under the same time conditions as before but in other groups of CCI-SN rats. Data in FIG. 9B show that the combined treatment with reboxetine+morphine was more effective than administration of either drug alone to increase pressure threshold value to trigger hindpaw withdrawal in the von Frey filaments test. However, calculation of corresponding AUC values indicated that the overall anti-allodynic effect of the combination of reboxetine+morphine [RM] was only 25% higher ($P>0.05$, NS) than the sum R+M of those induced by each drug administered alone (FIG. 9B). Accordingly, with 3.0 mg/kg s.c. of morphine, no evidence of synergy between the anti-allodynic effect of this opioid receptor agonist and that of reboxetine (10 mg/kg i.p.) could be evidenced.

In CCI-ION Rats

Figure 10:
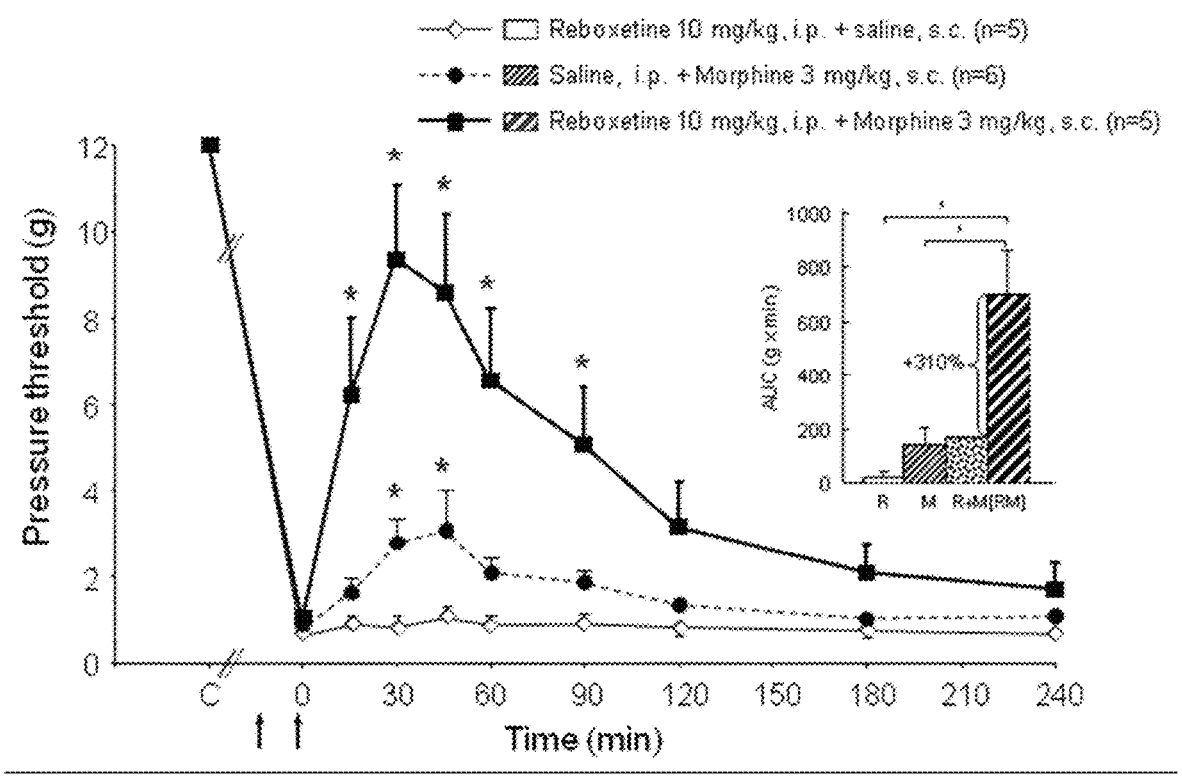
FIG. 10 shows the anti-allodynic effects of acute administration of reboxetine and morphine, alone or combined, in CCI-ION rats.

FIG. 10: Anti-Allodynic Effects of Acute Administration of Reboxetine and Morphine, Alone or Combined, in CCI-ION Rats.

Two weeks after unilateral chronic constriction injury to the infraorbital nerve, pressure threshold values (as g) to trigger nocifensive responses to von Frey filaments application onto ipsilateral vibrissal pad were determined at various times after injection of reboxetine (10 mg/kg i.p.) or saline, followed 15 min later by injection of morphine (3 mg/kg s.c.) or saline. Each point is the mean±S.E.M. of 5-6 independent determinations.

* $P<0.05$, compared to pressure threshold values determined in CCI-ION rats just prior to the second injection ($2^{nd}$ arrow, 0 on abscissa); Dunnett's test.

Bar diagrams: AUC values calculated from the respective time-course curves: R=reboxetine+saline; M=saline+morphine; [RM]=reboxetine+morphine. The third bar, R+M, corresponds to the sum of the first two bars, R and M.

* $P<0.05$, Student's t test.

For this series of experiments, morphine was used at the dose of 3 mg/kg s.c. because previous studies showed that the potency of morphine to alleviate neuropathic pain was much less in CCI-ION rats than in CCI-SN rats. Indeed, even at this dose which was clearly anti-allodynic in CCI-SN rats (see FIG. 8), morphine produced only a discrete effect in CCI-ION rats. At its maximum, the resulting increase in pressure threshold value only reached 20% of that determined in healthy intact rats (FIG. 10). On the other hand, reboxetine (10 mg/kg i.p.) was completely inactive on its own (FIG. 10). In contrast, the combination of reboxetine+morphine exerted a clear-cut anti-allodynic effect, which was markedly higher than that evoked by either drug alone. Indeed, AUC values showed that the overall effect of the combination of reboxetine+morphine [RM] was 310% higher than the sum R+M of the effects of each drug administered alone (FIG. 10).

The latter data strongly suggest that the synergy between morphine and reboxetine was not only present in CCI-ION rats but was even more pronounced than in CCI-SN rats.

Effects of Subchronic Treatment with Tapentadol on the Levels of mRNAs Encoding ATF3, IL-6 and BDNF in Ganglia and Central Tissues in CCI-SN- and CCI-ION-Rats Versus Respective Sham-Operated Rats In CCI-SN- Versus Sham-Rats Real-time qRT-PCR determinations of specific mRNA levels were made in tissues dissected from rats sacrificed 4 hours after the last injection of tapentadol or saline performed under the subchronic 5-day-treatment conditions (see Methods).

Figure 11:
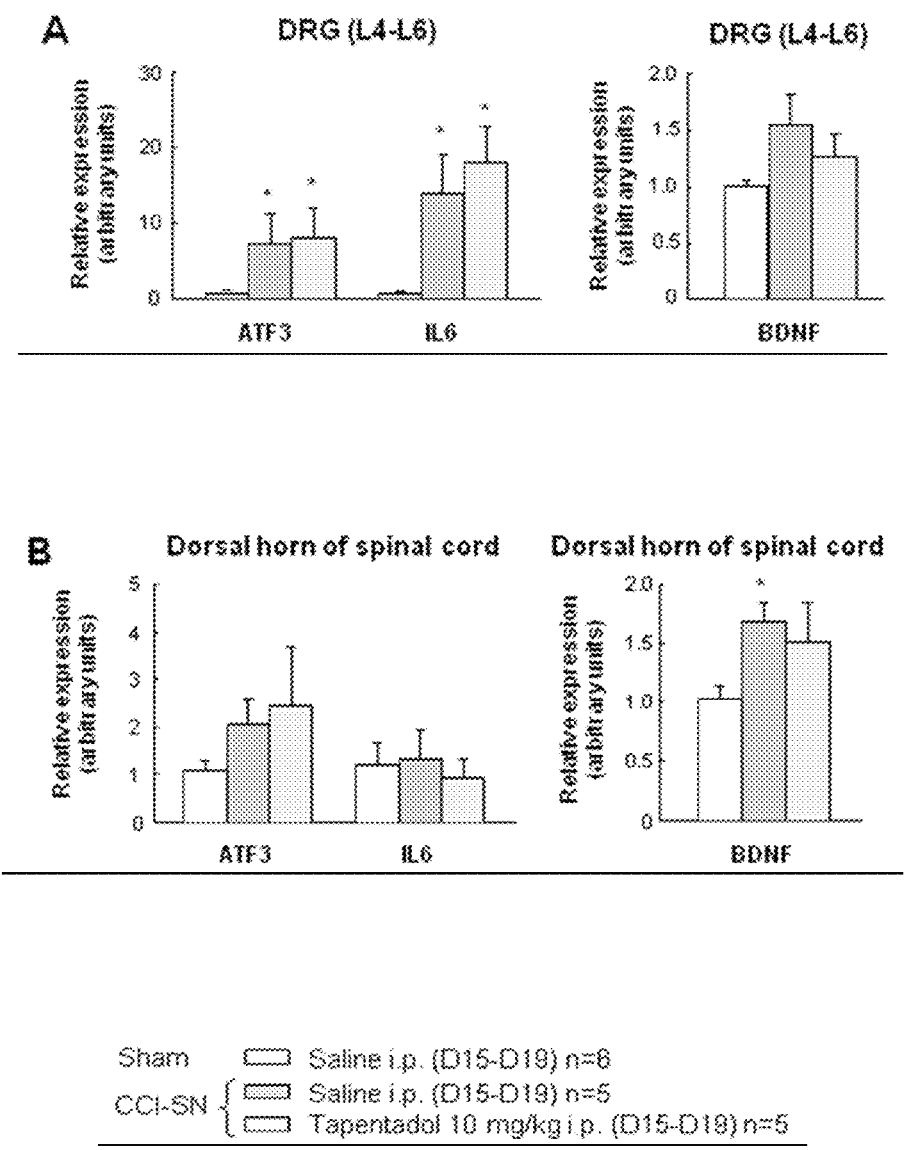
FIG. 11 depicts tissue levels of mRNA encoding ATF3, IL-6 and BDNF in (A) ipsilateral DRG (L4-L6) and (B) dorso-lateral quadrant of the lumbar enlargement in CCI-SN and sham-operated rats—effects of subchronic treatment with tapentadol.

FIG. 11: Tissue Levels of mRNA Encoding ATF3, IL-6 and BDNF in (A) Ipsilateral DRG (L4-L6) and (B) Dorso-Lateral Quadrant of the Lumbar Enlargement in CCI-SN and Sham-Operated Rats—Effects of Subchronic Treatment with Tapentadol.

Saline or tapentadol was administered to CCI-SN rats at days 15-19 under treatment conditions described in the legend to FIG. 6. Rats were decapitated 4 h after the last injection on day 19, tissues were immediately dissected in the cold (0° C.) and processed for mRNA extraction and quantification by real-time qRT-PCR. mRNA levels are expressed with reference to transcript encoding the reporter gene GaPDH. Each bar is the mean±S.E.M. of 5-6 independent determinations. * P<0.05, compared to respective mRNA levels in sham-operated rats treated with saline at days 15-19 after surgery, Newman-Keuls test. No significant differences were noted between tapentadol- and saline-treated CCI-SN rats.

Marked overexpression of ATF3 mRNA (by about seven-fold) and IL-6 mRNA (by about 15-fold) was found in ipsilateral (to the ligated sciatic nerve) L4-L6 DRG of CCI-SN rats compared to sham-operated animals (FIG. 11A). Higher BDNF-mRNA levels in CCI-SN rats were also observed in L4-L6 DRG (FIG. 11A), but this change was of lower amplitude (+56% over values in sham-operated rats) than those of ATF3 and IL-6 mRNAs and did not reach the critical level of statistical significance (P>0.05). In contrast, in the ipsilateral dorsal quadrant of the lumbar enlargement of the spinal cord at L4-L6, BDNF-mRNA levels were significantly higher (+66%, P<0.05) in CCI-SN- compared to sham operated-rats (FIG. 11B). On the other hand, no significant differences in ATF3 mRNA and IL-6 mRNA levels in this spinal cord area were found between sham-operated and CCI-SN rats (FIG. 11B). Also, on the contralateral side, none of these transcripts showed levels significantly different in nerve-ligated compared to sham-operated rats, both in DRG and the dorsal quadrant of the lumbar enlargement (not shown).

As illustrated in FIGS. 11A,B, levels of mRNA encoding ATF3, IL-6 and BDNF in both ipsilateral L4-L6 DRG and dorsal quadrant of the lumbar enlargement of the spinal cord were not significantly different whether CCI-SN rats had been treated subchronically with tapentadol or saline. These data suggest that, under the conditions used for subchronic treatment, tapentadol did not interfere with the overexpression of neuroinflammatory markers caused by CCI-SN.

In CCI-ION- Versus Sham-Rats

Figure 12:
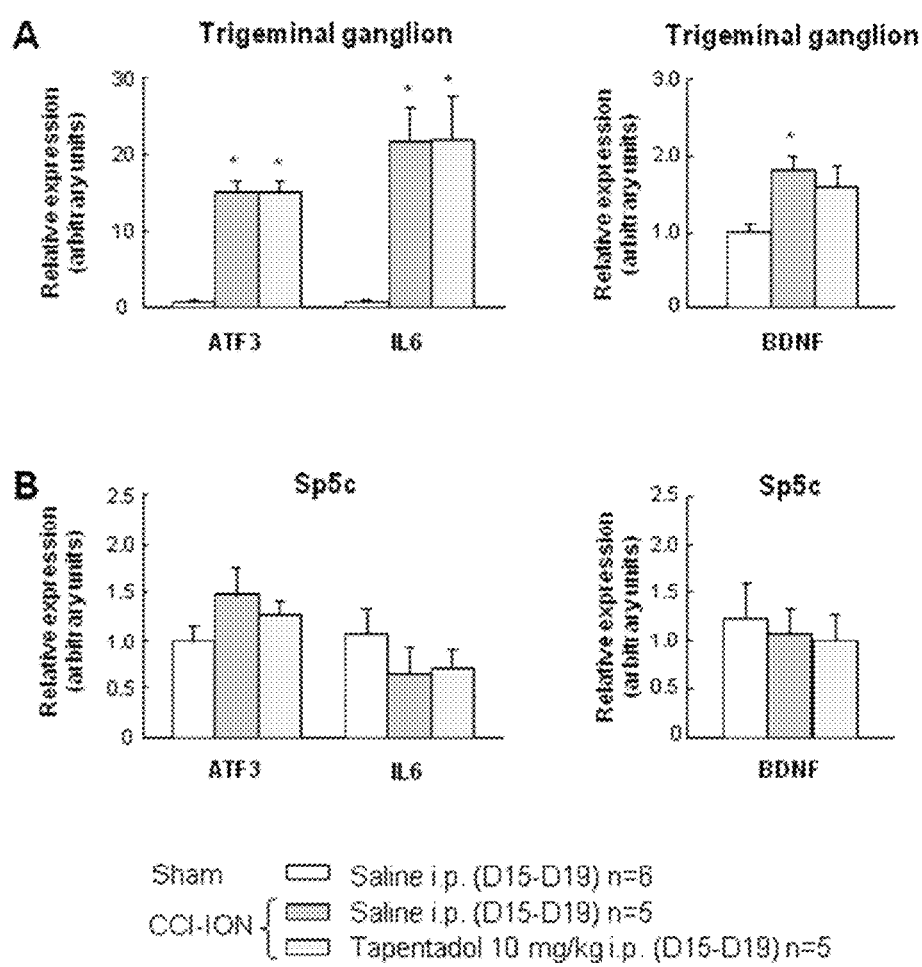
FIG. 12 depicts tissue levels of mRNA encoding ATF3, IL-6 and BDNF in (A) ipsilateral trigeminal ganglion and (B) caudal part of spinal trigeminal nucleus (Sp5c) in CCI-ION and sham-operated rats—effects of subchronic treatment with tapentadol.

FIG. 12: Tissue Levels of mRNA Encoding ATF3, IL-6 and BDNF in (A) Ipsilateral Trigeminal Ganglion and (B) Caudal Part of Spinal Trigeminal Nucleus (Sp5c) in CCI-ION and Sham-Operated Rats—Effects of Subchronic Treatment with Tapentadol.

Saline or tapentadol was administered to CCI-ION rats at days 15-19 under treatment conditions described in the legend to FIG. 6. Rats were decapitated 4 h after the last injection on day 19, tissues were immediately dissected in the cold (0° C.) and processed for mRNA extraction and quantification by real-time qRT-PCR. mRNA levels are expressed with reference to mRNA encoding the reporter gene GaPDH. Each bar is the mean±S.E.M. of 5-6 independent determinations. * P<0.05, compared to respective values in sham-operated rats treated with saline at days 15-19 after surgery, Newman-Keuls test. No significant differences were noted between tapentadol- and saline-treated CCI-ION rats.

Marked overexpression of ATF3 mRNA (by about 15-fold) and IL-6 mRNA (by more than 20-fold) was observed in the trigeminal ganglion on the lesioned side in CCI-ION-compared to sham-operated rats (FIG. 12A). In addition, BDNF mRNA was also upregulated (+82%) in the ipsilateral trigeminal ganglion of ION ligated- versus sham-rats, but to a lower extent than the other two mRNAs (FIG. 12A). In contrast, in the ipsilateral Sp5c area, the levels of mRNA encoding ATF3, IL-6 and BDNF did not differ between CCI-ION- and sham-rats (FIG. 12B). Similarly, no changes in the levels of these 3 specific mRNAs were noted in both the trigeminal ganglion and the Sp5c area on the side contralateral to infraorbital nerve ligature in CCI-ION rats compared to sham-operated animals (not shown). As noted above for DRG and spinal cord, subchronic treatment with tapentadol had no significant effects on ATF3, IL-6 and BDNF mRNA levels in both the trigeminal ganglion and the Sp5c area ipsilateral to nerve ligation in CCI-ION rats (FIG. 12A, B).

CONCLUSIONS

Acute administration of tapentadol (1-10 mg/kg, i.p.) significantly reduced allodynia in both CCI-SN and CCI-ION rats. Although morphine (3 mg/kg, s.c.) or reboxetine (10 mg/kg, i.p.) alone were only marginally active, the combination of both drugs produced supra-additive effects like those observed with tapentadol. Nerve ligation-induced overexpression of ATF3-, IL-6- and BDNF-transcripts in ipsilateral ganglia and/or central tissues was unchanged by subchronic antiallodynic treatment with tapentadol.

Antimigraine drugs such as triptans and CGRP receptor antagonists have clear-cut antiallodynic effects in CCI-ION rats. Because tapentadol also reduces mechanical allodynia in CCI-ION rats, there is indication that unexpectedly, tapentadol is also endowed with antimigraine properties.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of treating or inhibiting migraine in a subject suffering therefrom, said method comprising administering to said subject a medicament comprising an effective migraine treating or inhibiting amount of tapentadol, wherein tapentadol is the only therapeutically active ingredient in said medicament.

2. A method as recited in claim 1, wherein said subject is a subject suffering from moderate or severe pain.

3. A method as recited in claim 1, wherein the tapentadol is administered orally.

4. A method as recited in claim 1, wherein the tapentadol is administered once daily.

5. A method as recited in claim 1, wherein the tapentadol is administered twice daily.

6. A method as claimed in claim 1, wherein the tapentadol is administered at a daily dose within the range of from 25 to 600 mg.

* * * * *